United States Patent
Zhou et al.

(10) Patent No.: US 7,704,926 B2
(45) Date of Patent: *Apr. 27, 2010

(54) VISCOELASTIC COMPOSITIONS

(75) Inventors: Jian Zhou, Sugar Land, TX (US); Trevor Hughes, Cambridge (GB)

(73) Assignee: Schlumberger Technology Corporation, Ridgefield, CT (US)

( * ) Notice: Subject to any disclaimer, the term of this patent is extended or adjusted under 35 U.S.C. 154(b) by 551 days.

This patent is subject to a terminal disclaimer.

(21) Appl. No.: 10/250,415

(22) PCT Filed: Feb. 13, 2002

(86) PCT No.: PCT/GB02/00587
§ 371 (c)(1), (2), (4) Date: Dec. 15, 2003

(87) PCT Pub. No.: WO02/064945

PCT Pub. Date: Aug. 22, 2002

(65) Prior Publication Data

US 2004/0102330 A1    May 27, 2004

(30) Foreign Application Priority Data

Feb. 13, 2001   (GB) ................... 0103449.5

(51) Int. Cl.
C09K 8/584 (2006.01)
C09K 8/68 (2006.01)

(52) U.S. Cl. .............. 507/244; 507/129; 507/131; 507/132; 507/138; 507/240; 507/241; 507/245; 507/248; 507/260; 507/265; 507/267; 507/269; 166/308.2

(58) Field of Classification Search ............. 507/129, 507/239; 516/69
See application file for complete search history.

(56) References Cited

U.S. PATENT DOCUMENTS 2,715,108 A * 8/1955 Francis .............. 508/511

(Continued)

FOREIGN PATENT DOCUMENTS

CA  2407344 A1  11/2001

(Continued)

OTHER PUBLICATIONS

T.M. Muzyczko, S. Shore and J.A. Laboda, "Fatty Amidoamine Derivatives: N,N-Dimethl-N-(3-alkylamidopropyl)amines and Their Salts", Journal of the American Oil Chemists Society, 45 (Nov. 1968) 720-725.*

(Continued)

Primary Examiner—James Seidleck
Assistant Examiner—John J Figueroa
(74) Attorney, Agent, or Firm—James McAleenan; Vincent Loccisano; Brigid Laffey

(57) ABSTRACT

The present invention provides aqueous viscoelastic compositions comprising a cleavable surfactant and possibly also an electrolyte. The cleavable surfactants useful in the present invention comprise at least one weak chemical bond, which is capable of being broken under appropriate conditions, to produce oil soluble and water soluble products typically having no interfacial properties and surface activity compared with the original surfactant molecule. Further, the rheological properties of the aqueous viscolelastic composition are usually altered upon cleavage of the cleavable surfactant generally resulting in the elimination of the viscofying, viscoelastic and surfactant properties of the composition. Aqueous viscoelastic compositions in accordance with the present invention are suitable for use in oil-field applications, particularly for hydraulic fracturing of subterranean formations. Thus, the present invention also relates to a wellbore service fluid and a method of fracturing a subterranean formation. The present invention also concerns novel cleavable surfactants.

16 Claims, 8 Drawing Sheets

U.S. PATENT DOCUMENTS

| | | | | |
|---|---|---|---|---|
| 2,775,560 | A | * | 12/1956 | Westcott et al. ............. 508/212 |
| 2,836,560 | A | * | 5/1958 | Teale et al. ................. 508/136 |
| 3,762,932 | A | * | 10/1973 | Buddemeyer et al. ....... 426/554 |
| 3,886,293 | A | | 5/1975 | Zech |
| 4,853,138 | A | * | 8/1989 | Loza et al. .................. 507/211 |
| 5,171,476 | A | * | 12/1992 | Bloodworth et al. .......... 516/55 |
| 5,258,137 | A | | 11/1993 | Bonekamp et al. |
| 5,551,516 | A | * | 9/1996 | Norman et al. .......... 166/308.2 |
| 5,925,747 | A | | 7/1999 | Uphues et al. |
| 5,964,295 | A | | 10/1999 | Brown et al. |
| 5,979,555 | A | * | 11/1999 | Gadberry et al. ......... 166/270.1 |
| 5,979,557 | A | | 11/1999 | Card et al. |
| 6,239,183 | B1 | * | 5/2001 | Farmer et al. ............... 516/102 |
| 6,306,800 | B1 | | 10/2001 | Samuel et al. |
| 6,412,561 | B1 | | 7/2002 | Brown et al. |
| 6,435,277 | B1 | | 8/2002 | Qu et al. |
| 6,455,483 | B1 | * | 9/2002 | Carey ......................... 510/247 |
| 6,506,710 | B1 | | 1/2003 | Hoey et al. |
| 7,060,661 | B2 | | 6/2006 | Dobson et al. |
| 2002/0004464 | A1 | | 1/2002 | Nelson et al. |
| 2002/0069988 | A1 | * | 6/2002 | Yahiaoui et al. ............ 162/123 |

FOREIGN PATENT DOCUMENTS

| | | | |
|---|---|---|---|
| CA | 2434357 | A1 | 8/2002 |
| EP | 0 747 468 | A1 | 11/1996 |
| EP | 0 835 983 | A2 | 4/1998 |
| EP | 0 835 983 | A3 | 4/1998 |
| GB | 2 334 277 | A | 8/1999 |
| WO | 93/25648 | A1 | 12/1993 |
| WO | 94/09852 | A1 | 5/1994 |
| WO | 98/56497 | A1 | 12/1998 |
| WO | WO 99/32572 | * | 1/1999 |
| WO | 01/18147 | A1 | 3/2001 |
| WO | 01/77487 | A2 | 10/2001 |
| WO | 01/77487 | A3 | 10/2001 |

OTHER PUBLICATIONS

G.C. Maitland; "Oil and Gas Production", Current Opinion in Colloid & Interface Science, 5 (2000) 301-311.*

Raghavan, S.R. and Kaler, E.R., "Highly Viscoelastic Wormlike Micellar Solutions Formed by Cationic Surfactants with Long Unsaturated Tails", Langmuir 17 (2001) 300-306, published on Web Dec. 16, 2000 by ACS.*

Abstract of EP0747468 to Bimczok et al., "Aqueous Softeners for the Treatment of Textiles", Dec. 11, 1996 (in English).*

P.E. Hellberg, K. Bergstrom and K. Holmberg; Review entitled "Cleavable Surfactants"; Journal of Surfactants and Detergents; vol. 3, No. 1, Jan. 2000.*

Butler et al The hydrolysis of acetic anhydride. Part VII. Catalysis by pyridine and methylpyridines in acetate buffers Journal of the Chem. Society, 1961, pp. 4362-4367.

Fersht et al The acetylpyridinium ion intermediate in pyridine-catalyzed hydrolysis and acyl transfer reactions of acetic anhydride. Observation, kinetics, structure-reactivity correlations, and effects of concentrated salt solutions Journal of the American Chemical Society, vol. 92, 1970, pp. 5432-5442.

Holmberg Cleavable surfactants Novel Surfactants (Holmberg ed.), Marcel Dekker Inc, New York, 1998, pp. 333-358.

Kaiser et al Synthesis of esters of acid-unstable alcohols by means of $n$-butyllithium Journal of Organic Chemistry, vol. 35, No. 4, 1970, pp. 1198-1199.

Kivinen Mechanisms of substitution at the COX group The Chemistry of Acyl Halides (Patai ed.), Interscience Publishers, New York, 1972, pp. 177-230.

Krüger et al Esterquats Novel Surfactants (Holmberg ed.), Marcel Dekker Inc, New York, 1998, pp. 115-138.

Satchell An outline of acylation Quarterly Reviews of the Chem. Society, vol. 17, 1963, pp. 160-203.

Smith et al Aliphatic nucleophilic substitution March's Advanced Organic Chemistry, $5^{th}$ edition, Wiley-Interscience, New York, 2001, pp. 498-502, 506-514, 574-578.

Smith et al Aromatic electrophilic substitution March's Advanced Organic Chemistry, $5^{th}$ edition, Wiley-Interscience, New York, 2001, pp. 701-704.

Sommer et al Alkylation of amines. A general exhaustive alkylation method for the synthesis of quaternary ammonium compounds Journal of Organic Chemistry, vol. 36, No. 6, 1971, pp. 824-828.

Sommer et al Alkylation of amines. A new method for the synthesis of quaternary ammonium compounds from primary and secondary amines Journal of Organic Chemistry, vol. 35, 1970, pp. 1558-1562.

Yoneda et al A kinetic study of the reaction between sulfite ion and propylene oxide Journal of Organic Chemistry, vol. 40, No. 3, 1975, pp. 375-377.

* cited by examiner

VISCOELASTIC COMPOSITIONS

FIELD OF THE INVENTION

The present invention concerns viscoelastic compositions suitable for use in oil-field applications, particularly for hydraulic fracturing of subterranean formations.

Viscoelastic compositions are compositions having significant elastic properties such that when an applied stress is released, the composition exhibits a behaviour intermediate between the Hookean (elastic solid) and Newtonian (viscous fluid) extremes.

BACKGROUND OF THE INVENTION

Hydrocarbons such as oil, natural gas, etc. are obtained from a subterranean geologic formation (e.g. a "reservoir") by drilling a well that penetrates the hydrocarbon-bearing formation. This provides a partial flowpath for the hydrocarbon, typically oil, to reach the surface. In order for oil to be "produced", that is, travel from the formation to the wellbore (and ultimately to the surface), there must be a sufficiently unimpeded flowpath through the formation rock (e.g. sandstone, carbonates), which generally occurs when rock pores of sufficient size and number are present.

A common reason for a decline in oil production is "damage" to the formation, which plugs the rock pores and impedes the flow of oil. Often such damage can be attributed to a number of factors including, the methods and chemicals used in establishing the well, remedial operations performed on the well, or the formation being naturally "tight" (e.g. a low permeability formation), with pores sufficiently small that the oil migrates toward the wellbore only very slowly.

Generally, techniques used to increase the permeability of the formation are referred to as "stimulation". Stimulation of the formation can be performed by: (1) injecting chemicals into the wellbore to react with and/or dissolve damage; (2) injecting chemicals through the wellbore and into the formation to react with and/or dissolve small portions of the formation to create alternative flowpaths for the hydrocarbon; or (3) injecting chemicals through the wellbore and into the formation at pressures sufficient to fracture the formation, thereby creating a channel through which hydrocarbon can more readily flow from the formation and into the wellbore.

Hydraulic fracturing involves breaking or fracturing a portion of the surrounding strata of the formation, by injecting a specialised fluid into the wellbore directed at the face of the formation at pressures sufficient to initiate and extend a fracture in the formation. Typically, the process creates a fracture zone, that is, a zone in the formation having multiple fractures, through which hydrocarbon can more easily flow to the wellbore.

Typical fracturing treatments e.g. fluids, generally comprise at least three components; a carrier fluid (usually water or brine), a polymer, and a proppant. Many further comprise a crosslinker. Other compositions used as fracturing fluids include water with additives, and gelled oils. The purpose of these fracturing fluids is to firstly create and extend a fracture, and then once it is opened sufficiently, deliver proppant into the fracture via the carrier fluid, which keeps the fracture from closing once the pumping operation is completed.

Viscoelastic compositions have also been found to be usefully employed as fracturing fluids. Conveniently, use has been made of surfactants which when in an aqueous solution are capable of forming a viscoelastic composition for this purpose. Such surfactants are referred to herein for brevity and simplicity as "viscoelastic surfactants". The utility of fracturing fluids comprising viscoelastic surfactants has been attributed to the Theological properties of the fluid compositions, the stability of such fluids and their low residue content.

Conventional surfactants, specifically those which tend to form spherical micelles, are generally not capable of forming a viscoelastic composition, particularly an aqueous viscoelastic composition, and are thus not suitable for use in a hydraulic fracturing application. However, certain surfactants, specifically those which tend to form long rod-like or worm-like micelle structures, e.g. viscoelastic surfactants, are capable of forming an aqueous viscoelastic composition which is readily applicable in hydraulic fracturing. At a relatively low total concentration of a viscoelastic surfactant, typically in the range 1 to 10 wt %, these long rod-like or worm-like micelle structures overlap, forming an entangled network which is viscoelastic. Typically, these large micelle structures are readily destroyed by their interaction with formation fluids such as hydrocarbon fluids. When the micellar structures are broken by their interaction with the hydrocarbon fluid, a solution with low viscosity is formed. Thus, as the viscoelastic surfactant based fracturing fluid interacts with produced hydrocarbon fluids, a dramatic change in micellar structure (from rod-like or worm-like to spherical micelles) for instance causes a dramatic change in the rheological properties of the fracturing fluid (from a viscoelastic composition to an inviscid solution). It is this "responsive" fluid which facilitates easy removal and clean up of the fluid from the propped fracture so as to maximise hydrocarbon production.

The application of viscoelastic surfactants in both non-foamed and foamed fracturing fluids has been described in several patent specifications.

U.S. Pat. No. 5,258,137 relates to foam fluid compositions, which are described as stable over a range of temperatures, easily formulated and possessing good shear stability, and which comprise an aqueous liquid, a thickening amount of a viscoelastic surfactant e.g. including those represented by the following formula.

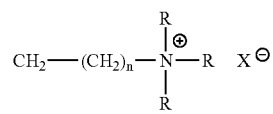

and a functionally effective amount of a surfactant which is capable of forming a foam.

U.S. Pat. No. 5,551,516 describes a hydraulic fracturing fluid comprising an aqueous base fluid e.g. water, a thickener selected from a specified group, an inorganic water soluble salt, at least one viscoelastic surfactant for suspending a proppant during placement, and a stabilising organic salt or $C_4$ to $C_{12}$ alcohol. The fracturing fluid is stated to find application in the fracturing treatment of high permeability subterranean formations.

U.S. Pat. No. 5,964,295 describes methods for, (i) reducing fracturing fluid loss into a relatively low permeability formation during fracturing, (ii) enhancing the cleanup of a fracturing fluid from a well and reducing the production of water from a subterranean formation, and (iii) reducing the equipment required to mix and pump fracturing fluids, by employing a fracturing fluid containing a viscoelastic surfactant. In a further described method, an aqueous viscoelastic surfactant based hydraulic fracturing fluid comprising an aqueous based thickener, a water soluble salt, and at least one amine or salt of an amine thickener, is used to fracture a formation.

U.S. Pat. No. 5,979,557 relates to a method for acidizing a formation, and to a method for limiting the inflow of formation water during and after a well turn around, to maximise recovery of the hydrocarbons and fracturing fluid, the methods comprising a step of, selectively blocking the pore structure of the formation face in the water-bearing zone, but not in the hydrocarbon zone. In a preferred embodiment, the pore structure is blocked by a plug of viscous fluid, which comprises amongst other components, a viscoelastic surfactant which is capable of forming worm-like micelles in an aqueous environment.

A potential disadvantage associated with the use of the viscoelastic surfactants of the prior art, is the tendency of the individual viscoelastic surfactant molecules to form emulsions with the formation fluid (i.e. the hydrocarbon to be extracted) following fracturing. Emulsion droplets formed within the fracture or within the invaded matrix zones may produce a barrier to formation fluid flow which may limit fluid clean up and hydrocarbon production.

SUMMARY OF THE INVENTION

According to one aspect of the present invention, there is provided an aqueous viscoelastic composition comprising a cleavable surfactant.

The term "cleavable surfactant" as used herein means a surfactant having at least one weak chemical bond within the molecule, which may be broken at a controlled rate under appropriate conditions of temperature and/or pH, to produce smaller fragments of the molecule. A cleavable surfactant may also be referred to as a "degradable", "temporary", or "self-destructive" surfactant.

Following cleavage of at least one weak chemical bond comprising the cleavable surfactant, the rheological properties e.g. viscosity of an aqueous viscoelastic composition are usually altered. The cleavage or breakdown products of the cleavable surfactant, are typically either more soluble in oil, or more soluble in water, than the original surfactant molecule. Therefore, the breakdown products have no interfacial properties and are non-surface active in comparison with the surfactant molecule. Thus, cleavage of the cleavable surfactants comprising an aqueous viscoelastic composition in accordance with the present invention, eliminates viscosifying, viscoelastic and surfactant properties of said composition, thereby reducing the potential of a surfactant to form emulsions with a fluid such as for example, a hydrocarbon-containing formation fluid. Advantageously, therefore, aqueous viscoelastic compositions according to the present invention are suitable for application in a wellbore service fluid, particularly a hydraulic fracturing fluid for fracturing subterranean formations, or a well clean-out fluid, where the compositions of the present invention obviate the difficulties encountered with the non-cleavable viscoelastic surfactants of the prior art. Conveniently, the elimination of the viscosifying, viscoelastic and surfactant properties of an aqueous viscoelastic composition as outlined above, facilitates the easy removal and clean-up of a fluid from the propped fracture and additionally reduces the potential of a surfactant to form unwanted, stable emulsions. Moreover, generally, as the weak chemical bond of the cleavable surfactant can be broken under appropriate conditions, the rate of conversion from a viscoelastic composition to a low viscosity solution can be controlled, and therefore the efficiency with which the wellbore service fluid may be removed by the formation fluid is typically improved.

The aqueous viscoelastic compositions of the present invention may suitably be in the form of a solution, or gel, and the like.

Typically, a cleavable surfactant will be added to an aqueous composition e.g. water. Generally, the form of this composition may alter with the addition of optional additives e.g. electrolytes, where the term "electrolyte" as used herein means a compound which undergoes partial or complete dissociation into ions in solution. Preferably, a source of electrolytes is added to a composition comprising a cleavable surfactant to increase the viscosity of the composition so that for example, the composition forms a gel.

Thus, according to a further aspect of the present invention, there is provided an aqueous viscoelastic composition comprising a cleavable surfactant and an electrolyte.

Therefore, in a preferred embodiment herein, generally, the aqueous viscoelastic composition comprises a sufficient quantity of electrolyte, being at least one inorganic or organic water soluble salt, or mixtures thereof.

Typical inorganic water soluble salts suitable for use herein include alkali metal salts and the like such as potassium and ammonium salts e.g. potassium chloride, tetramethyl ammonium chloride and ammonium chloride; alkaline earth metal halides such as calcium chloride, calcium bromide and magnesium chloride; transition metal salts such as zinc halide salts, aluminium salts, zirconium salts and the like; and salts which dissolve in aqueous solution to release divalent anions such as for example sulfate or carbonate anions etc.

Suitable organic water soluble salts for use herein typically involve a sodium or potassium salt of an organic anion. The anion may be an aromatic organic anion such as a salicylate, naphthalene sulfonate, p-and m-chlorobenzoates, 3,5 and 3,4 and 2,4-dichlorobenzoates, t-butyl and ethyl phenate, 2,6 and 2,5-dichlorophenates, 2,4,5-trichlorophenate, 2,3,5,6-tetrachlorophenate, p-methyl phenate, m-chlorophenate, 3,5,6-trichloropicolinate, 4-amino-3,5,6-trichloropicolinate, 2,4-dichlorophenoxyacetate, toluene sulfonate, a,b-napthols, pp-'bisphenol A or cocoamidopropyl dimethyl amine oxide.

Preferably, the electrolyte is an inorganic water soluble salt, preferably an alkali metal salt and more preferably a potassium salt.

The optimum choice of electrolyte is determined by the structure and properties of the cleavable surfactant and is normally chosen such that the strength and temperature tolerance of the aqueous viscoelastic composition, typically a gel, is maximised. Additionally, an electrolyte is chosen which is compatible with the counterion of the cleavable surfactant so that undesirable precipitates are not formed. The concentration at which an electrolyte is employed is typically dependent upon the nature of the electrolyte and the type of cleavable surfactant.

Whether a composition according to the present invention can be described as viscoelastic depends on a number of factors which include for example, the concentration of the cleavable surfactant, the nature of the cleavable surfactant, and the type and concentration of the electrolyte. A determination of whether any particular aqueous composition is viscoelastic will be readily determined by a person skilled in the art employing a suitable test for viscoelasticity.

For example, the viscoelasticity of an aqueous composition may be measured by carrying out dynamic oscillatory theological measurements on the composition as generally described in Barnes H. A. et at., *An Introduction to Rheology*, Elsevier, Amsterdam (1997). In a typical dynamic oscillatory experiment, the composition is sheared sinusoidally according to the following equation (1):

$$\gamma(t) = \gamma_{(max)} \sin \omega t \quad (1)$$

Where $\gamma(t)$ is the strain, $\gamma(max)$ is the maximum strain, t is time and $\omega$ is the angular frequency. The shear stress, $\sigma$, is given by:

$$\sigma(t) = \sigma_{(max)} \sin (\omega t + \delta) \quad (2)$$

where $\delta$ is the phase angle.

The relative inputs given by the elastic component (G') and viscous component (G") are resolved as follows. Expanding the sine function in equation (2) gives equations (3) and (4) as follows:

$$\sigma(t) = \sigma_{(max)}[\sin \omega t \cos\delta + \cos \omega t \sin \delta] \quad (3)$$

$$\sigma(t) = \gamma_{(max)}[G' \sin \omega t + G'' \cos \omega t] \quad (4)$$

where $G' \equiv (\sigma_{(max)}/\gamma_{(max)}) \cos \delta$ and $G'' \equiv (\sigma_{(max)}/\gamma_{(max)}) \sin \delta$.

Equation (4) therefore defines two dynamic moduli: G', the storage modulus or elastic component and G", the loss modulus or viscous component of a composition having viscoelastic properties.

Preferably, the aqueous viscoelastic composition of the present invention is an aqueous viscoelastic gel, where the term "viscoelastic gel" as used herein means a composition in which the elastic component (G') is at least as important as the viscous component (G"). In the evolution from a predominantly viscous liquid to a viscoelastic gel, the gel point can be defined by the time when the contribution from the elastic and viscous components becomes equal, i.e. G'=G"; at and beyond this point in time, G'$\geq$G" and the phase angle, $\delta$ is $\geq 45°$.

Cleavable surfactants useful herein are capable of forming rod-shaped or worm-like micelles as opposed to spherical micelles or sheet-like structures, therefore they may be referred to as cleavable, viscoelastic surfactants. The formation of these rod-shaped micellar structures typically increases the viscosity of an aqueous composition comprising the surfactants which are generally present in the composition at a concentration in the range 1% to 10% by weight, such that viscoelastic properties are imparted to the composition. The ability of a surfactant to form worm-like micelles and to impart viscoelastic properties to an aqueous composition depends on a number of factors, as has been described hereinabove.

Further, cleavable surfactants useful in the compositions of the present invention generally have the ability to form rod-shaped micelle structures over a broad range of concentrations. Generally, an aqueous viscoelastic composition according to the present invention comprises from about 1% to about 10% by weight of the composition of a cleavable surfactant.

Cleavable surfactants useful herein typically comprise a hydrophobic group linked to a hydrophilic group via a weak chemical bond, referred to herein after for brevity and simplicity as a "linkage". The linkage is such that it may be cleaved under certain conditions e.g. temperature and pH, at a desired and appropriate time, to produce at least one oil soluble and at least one water soluble product.

In general terms, the hydrophobic group is usually a linear or branched hydrocarbon chain which is either fully saturated or partially unsaturated.

The hydrophilic groups are usually positively charged, negatively charged or zwitterionic.

Typically, the linkage is suitably an acetal, amide, ether or ester group, although other groups having weak chemical bonds, which can be broken for example by hydrolysis at a controlled rate, under acid or alkaline conditions may be possible. Preferably, the linkage is an acetal, amide or ester group.

Cleavable surfactants useful herein may be cationic, anionic or zwitterionic.

Cleavable surfactants, as such, are known for use for example in detergent and personal care products such as fabric softeners and hair conditioners as described in *Novel Surfactants*, edited by K. Holmberg, Marcel Dekker Inc., New York, (1998), ISBN:0-8247-0203-4, see Chapters 4 and 11 pp 115-138 and 333-358 respectively. However, there is no discussion of such surfactants being used to formulate viscoelastic compositions, particularly viscoelastic gels, as the formation of these types of structures would generally be undesirable in such product types.

Examples of suitable cationic cleavable surfactants (some of which are novel per se as will be discussed hereinafter) useful in the aqueous viscoelastic compositions of the present invention include surfactants shown by the following formulae:

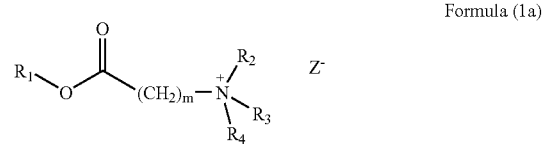

Formula (1a)

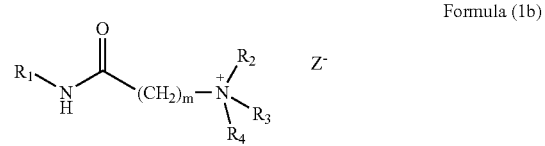

Formula (1b)

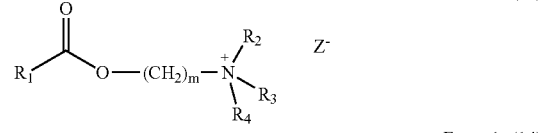

Formula (1c)

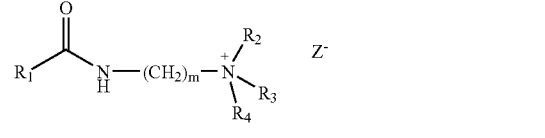

Formula (1d)

Examples of suitable anionic cleavable surfactants (some of which are novel per se as will be discussed hereinafter) useful in the aqueous viscoelastic compositions of the present invention include surfactants shown by the following formulae:

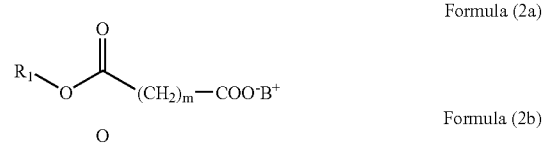

Formula (2a)

Formula (2b)

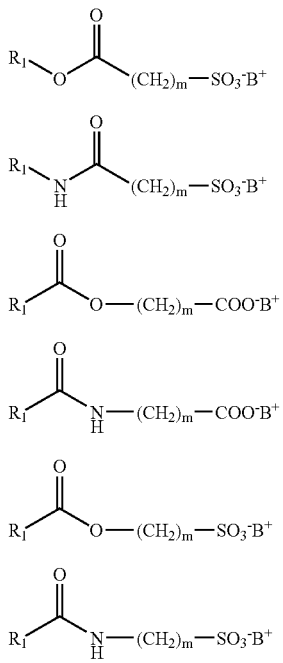

Formula (2c)

Formula (2d)

Formula (2e)

Formula (2f)

Formula (2g)

Formula (2h)

Examples of suitable zwitterionic cleavable surfactants (some of which are novel per se as will be discussed hereinafter) useful in the aqueous viscoelastic compositions of the present invention include surfactants shown by the following formulae:

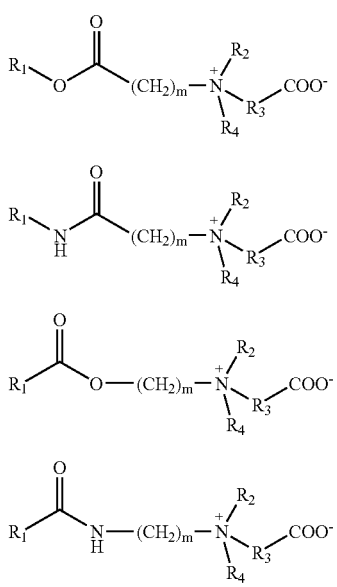

Formula (3a)

Formula (3b)

Formula (3c)

Formula (3d)

where $R_1$ is a saturated or unsaturated, linear or branched aliphatic chain of at least 18 carbon atoms; m is at least one, preferably m is at least two, and when m is $\geq 3$, m may be a straight or branched alkyl chain; $R_2$ and $R_4$ are each independently hydrogen, or a linear or branched saturated aliphatic chain of at least 1 carbon atom, preferably a $CH_3$ or a $CH_2CH_3$ group, or a linear or branched saturated aliphatic chain of at least 1 carbon atom with one or more of the hydrogen atoms replaced by a hydroxyl group, e.g. —$CH_2CH_2OH$ (hydroxyethyl); when the cleavable surfactant is cationic, $R_3$ may be the same as $R_2$ and/or $R_4$; when the cleavable surfactant is a zwitterion, $R_3$ is a linear or branched saturated aliphatic chain of at least 1 carbon atom; $Z^-$ and $B^+$ are ionic counterions where typically, for example, $Z^-$ is a monovalent anion such as a halide, perchlorate or nitrate etc. or a divalent anion such as a sulfate or carbonate etc. and $B^+$ is hydrogen or a monovalent cation such as an alkali metal ion and the like e.g. potassium or sodium etc.

The cleaved products of a cleavable surfactant generally comprise at least one water-soluble and one water-insoluble product.

When the linkage of a cleavable surfactant is an amide or ester group, the carbonyl carbon atom may be positioned closer to the hydrophilic group e.g. an O(CO) or HN(CO) group, thereby forming 'reverse' esters or amides. These types of cleavable surfactants containing reverse esters or amides (typically represented by formulae 1(a)-(b), 2(a)-(d) and 3(a)-(b) above) may be cleaved to give (i) a water-insoluble alcohol or amine product, e.g. a long chain alcohol R1-OH, or long chain amine, $R_1$-$NH_2$ and (ii) a water-soluble acid product e.g. $HOOC(CH_2)_m N^+ R_2 R_3 R_4$, $HOOC(CH_2)_m COO^-$, $HOOC(C_2)_m SO_3^-$ or $HOOC(CH_2)_m N^+ R_2 R_4 R_3 COO^-$.

Alternatively, when the carbonyl carbon atom of an ester or amide linkage is positioned away from the hydrophilic group e.g. a (CO)O or (CO)NH group, such surfactants (typically represented by formulae 1(c)-(d), 2(e)-(h) and 3(c)-(d) above) may be cleaved to give (i) a water-insoluble acid product e.g. a long chain carboxylic acid $R_1$—COOH and (ii) a water-soluble alcohol or amine type product e.g. E-$(CH_2)_m$—F where E is OH (ester version) or $NH_2$ (amide version) and F is $R_2 R_3 R_4 N^+$ (cationic cleavable surfactants), $COO^-$ or $SO_3^-$ (anionic cleavable surfactants) or $R_2 R_4 N^+ R_3 COO^-$ (zwitterionic cleavable surfactants).

Cleavable surfactants useful in the aqueous viscoelastic compositions described herein may be prepared according to a number of synthetic routes.

In one approach, a cleavable surfactant may be synthesised by coupling either a long chain alcohol or amine with a carboxylic acid anhydride or a carboxylic acid halide having a hydrophilic group e.g. $R_2 R_3 R_4 N^+ Z^-$ attached at the opposite end of the hydrocarbon chain e.g —$(CH_2)_m$– as described in March J. *Advanced Organic Chemistry*, $3^{rd}$ Edition, John Wiley & Sons, New York (1985); Kaiser et al., *Journal of Organic Chemistry*, 1970, 35, 1198; Kivinen, in Patai, *The Chemistry of Acyl Halides*, pp 177-230, Interscience, New York (1972); Satchell, Q. *Rev. Chem. Soc.* 1963, 17, 160-203; Butler et al. *J. Chem. Soc.* 1961, p 4362; Fersht et al. *J. Am. Chem. Soc.* 1970, 92, 5432; and Challis and Challis, in Zabicky, *The Chemistry of Amides*, Interscience, New York (1970); all of which are incorporated herein by reference. Two typical and representative examples of such reactions are outlined below:

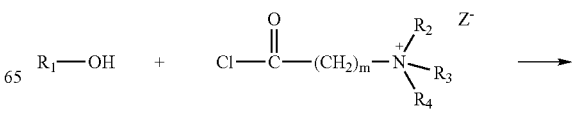

-continued

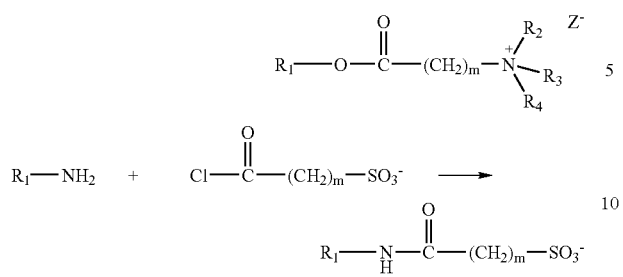

$R_1-NH_2$ +  ⟶

Alternatively, a cleavable surfactant can be synthesised by coupling either a carboxylic acid or carboxylic acid halide with an alcohol or amine having a hydrophilic group e.g. $CO_2^-$, $SO_3^-$ etc. attached at the opposite end of the hydrocarbon chain e.g. $-(CH_2)_{m-}$. Three typical and representative examples of such reactions are outlined below:

$R_1COCl$ + $HO(CH_2)_mCO_2H$ ⟶

-continued

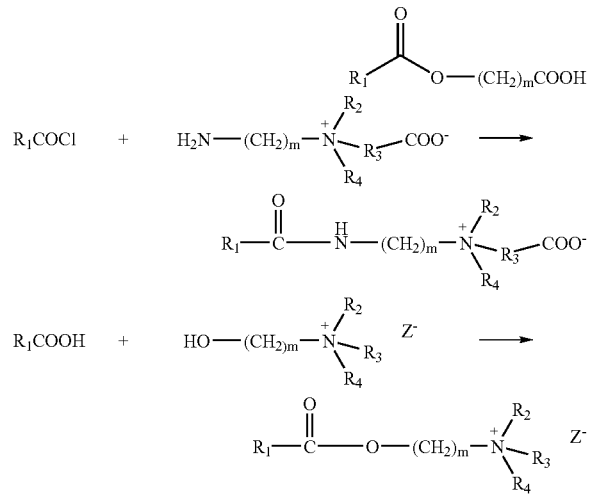

In an even further approach, a cleavable surfactant useful herein can be synthesised by a multiple stage approach as illustrated in the following reaction scheme:

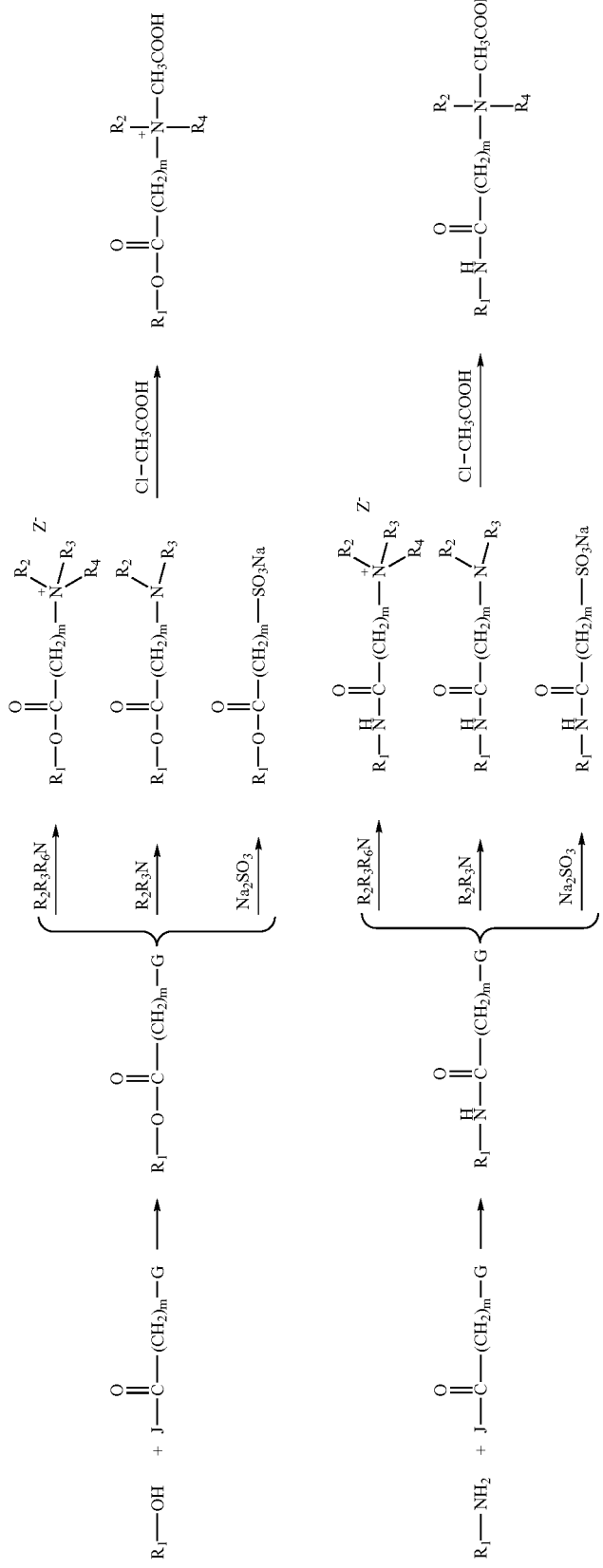

where J is independently selected from Cl, Br, I or OH and G is Cl, Br or I.

Stage 1 involves coupling either an alcohol or amine with a carboxylic acid anhydride or carboxylic acid halide type compound as described in March J. *Advanced Organic Chemistry*, 3$^{rd}$ Edition, John Wiley & Sons, New York (1985). The product of stage 1 is then reacted with an appropriate amine to produce a cationic cleavable surfactant or zwitterionic intermediate cleavable surfactant, as described in March J. *Advanced Organic Chemistry*, 3$^{rd}$ Edition, John Wiley & Sons, New York (1985); Sommer et al. *J. Org. Chem.*, 1971, 36, 824; Sommer et al. *J. Org. Chem.*, 1970, 35, 1558; Spialter and Pappalardo, *The Acyclic Aliphatic Tertiary Amines*, Macmillan, New York, (1965). Alternatively, the product of stage 1 is reacted with sodium sulphite to produce an anionic cleavable surfactant as described in March J. *Advanced Organic Chemistry*, 3$^{rd}$ Edition, John Wiley & Sons, New York (1985); Gilbert, *Sulfonation and Related Reactions*, Interscience, New York, (1965); Yoneda et al. *J. Org. Chem.*, 1975, 40, 375. A zwitterionic cleavable surfactant is produced at stage 3 by further reacting the intermediate amine product of stage 2 with a carboxylic acid halide.

Typically, the rate at which the linkage of the cleavable surfactant can be broken is dependent upon the pH of the aqueous viscoelastic composition and the temperature. Under the appropriate conditions therefore, as the cleavable surfactants are degraded, the aqueous viscoelastic composition loses its viscoelasticity, such that the contribution from the elastic modulus (G') in the composition becomes less than that of the viscous modulus (G"). The resulting composition is therefore a low viscosity fluid exhibiting near-Newtonian or Newtonian behaviour, Typically therefore, the rate of conversion of an aqueous viscoelastic composition to a low viscosity fluid can be controlled and is generally dependent upon the decomposition rate of the cleavable surfactants.

Generally, for any of the above-mentioned cleavable surfactants, the higher the temperature, the faster the rate of cleavage of the cleavable surfactant. Specifically, when the linkage of a cleavable surfactant is an ester group, the decomposition rate attains a maximum under high pH (alkaline) conditions. Conversely, for cleavable surfactants comprising as the linkage an amide group, the decomposition rate is at a maximum under low pH (acidic) conditions. Low pH that is to say acidic, conditions can also be used to cleave cleavable surfactants when the linkage is an acetal.

In general, the oil-soluble and water-soluble products produced from a cleavable surfactant, are not themselves capable of producing a viscoelastic composition. For cleavable surfactants comprising as the degradable linkage, an ester or amide group, two main types have been described above: those which degrade to give a long chain alcohol or amine, and those which degrade to give a long chain carboxylic acid. Typically, long chain alcohols are not known to form viscoelastic compositions. Similarly, long chain amines do not typically form viscoelastic compositions. However, long chain carboxylic acids may form viscoelastic compositions when in the deprotonated form; therefore, in designing a composition using the cleavable surfactants shown for example, in formulae 1(c)-(d), 2(e)-(h) and 3(c)-(d) above, it is generally important to ensure that acidic conditions are maintained after cleavage of the surfactant.

The aqueous viscoelastic compositions of the present invention may optionally comprise additional viscoelastic surfactants as described for example in U.S. Pat. No. 5,258, 137; U.S. Pat. No. 5,551,516; U.S. Pat. No. 5,964,295 and U.S. Pat. No. 5,979,557; all of which are hereby incorporated by reference.

The aqueous viscoelastic compositions according to the present invention are preferably a wellbore service fluid, more preferably a hydraulic fracturing fluid, or a well clean-out fluid, and even more preferably an aqueous fracturing fluid. The invention thus provides a wellbore service fluid comprising an aqueous viscoelastic composition in accordance with the invention.

To prepare a wellbore service fluid, particularly a hydraulic fracturing fluid, or a well clean-out fluid, more particularly an aqueous fracturing fluid, the cleavable surfactant is generally added to an aqueous solution in which has been dissolved a quantity of electrolyte, typically at least one inorganic or organic water soluble salt. If fluid density becomes an important consideration, heavier electrolytes may be employed. Standard mixing procedures known in the art can be employed since heating of the solution and special agitation conditions are normally not necessary. Of course, if used under conditions of extreme cold such as found in Alaska or Canada, normal heating procedures should be employed.

Sometimes it is preferable to dissolve the cleavable surfactant into a lower molecular weight alcohol prior to mixing it with the aqueous solution. The lower molecular weight alcohol or diol, for instance isopropanol or propylene glycol, may function to liquify the surfactant concentrate and therefore aid the solubilisation of the cleavable surfactant on mixing with the aqueous solution, Other similar agents may also be employed. Further, a defoaming agent such as a polyglycol may be employed to prevent undesirable foaming during the preparation of the fracturing fluid if a foam is not desirable under the conditions of the treatment. If a foamed fluid is desired, a gas such as air, nitrogen, carbon dioxide or the like may be employed.

In addition to the electrolytes and cleavable surfactants described herein, the wellbore service fluid may contain other conventional constituents which perform specific desired functions, e.g., corrosion inhibitors, fluid-loss additives, and others as described previously herein, and the like. A proppant can then be suspended in the wellbore service fluid.

Generally, in use, the micellar structures formed by the cleavable surfactants and the interactions between such micellar structures of the wellbore service fluid are readily altered by shear rate conditions, the presence of hydrocarbons, or by increased temperature. All of these features may be found in the hydrocarbon portion of the reservoir. Typically, the cleavable surfactant worm-like micelle structures are destroyed as they interact with the fluids produced from the hydrocarbon-bearing formation. At this stage, the worm-like micellar structures are no longer required to impart the high viscosity required to transport particles such as the proppant into the fracture. Additionally, after a period of time the cleavable surfactant molecules conveniently decompose to form breakdown products which are either soluble in water or soluble in oil. The oil-soluble products may be extracted with the produced hydrocarbon fluids and the water-soluble products with the produced water.

Therefore, according to an even further aspect of the present invention, there is provided a method of fracturing a subterranean formation, comprising the steps of:

(A) providing a wellbore service fluid comprising a cleavable surfactant, and (B) pumping the fluid through a wellbore and into a subterranean formation at a pressure sufficient to fracture the formation.

As mentioned hereinabove, some of the previously described cleavable surfactants are novel per se.

Thus, according to an even further aspect of the present invention, there is provided a cleavable surfactant having the structure of formula 1, formula 2 or formula 3:

$$R_1—X—(CR_5R_6)_m—Y^{\oplus}Z^{\ominus} \quad \text{Formula 1}$$

or $$R_1-X-(CR_5R_6)_m-A^{\ominus}B^{\oplus} \quad \text{Formula 2}$$

or $$R_1-X-(CR_5R_6)_m-Y^{\oplus}-A^{\ominus} \quad \text{Formula 3}$$

where (i) $R_1$ is a saturated or unsaturated, linear or branched aliphatic chain of at least 18 carbon atoms;
(ii) X is an O(CO), (CO)O, $R_7$N(CO), or (CO)$NR_7$ group;
(iii) m is at least one;
(iv) $Y^{\oplus}$ is —$NR_2R_3R_4$;
(v) $R_2$, $R_3$, $R_4$, $R_5$, $R_6$ and $R_7$ are each independently hydrogen; a linear or branched, saturated aliphatic chain of at least 1 carbon atom; or a linear or branched, saturated aliphatic chain of at least 1 carbon atom with one or more of the hydrogen atoms replaced by a hydroxyl group, wherein for cleavable surfactants of formula 3, the R group linked to $A^{\ominus}$ is not hydrogen;
(vi) $A^{\ominus}$ is a sulfonate or carboxylate anionic group; and
(vii) $Z^{\ominus}$ and $B^{\oplus}$ are ionic counterions associated with a cleavable surfactant of formula 1 or formula 2, where $Z^{\ominus}$ is a monovalent anion or divalent anion and $B^{\oplus}$ is hydrogen or a monovalent cation, excluding surfactants of formula 1 in which X is O(CO), $R_5$ and $R_6$ are each independently hydrogen, m is one and $Y^{\oplus}$ is —$NR_2R_3R_4$.

Preferably, $R_1$ is an aliphatic chain of at least 20 carbon atoms and more preferably at least 22 carbon atoms. Generally, there are no constraints on the maximum chain length of $R_1$, provided that the cleavable surfactant as an entity is water-soluble in an aqueous composition.

Preferably, m is at least two, and when m is $\geq 3$, m may be a straight or branched alkyl chain.

Suitable monovalent anions for $Z^{\ominus}$ include for example a halide, perchlorate or nitrate ion and suitable divalent anions for $Z^{\ominus}$ include for example sulfate and carbonate ions.

Suitable monovalent cations for $B^{\oplus}$ include for example alkali metal ions and the like such as potassium or sodium etc.

Examples of cleavable surfactants in accordance with formula 1, formula 2 or formula 3 include N,N-dimethyl N-ethyl glycine erucyl ester chloride and monooleyl succinic acid or derivatives threreof.

The invention will be described, by way of illustration, in the following non-limiting examples, and with reference to the accompanying drawings, in which:

FIG. 1 is a graph showing the viscoelastic properties, particularly the elastic modulus (G') and the viscous modulus (G") of an aqueous viscoelastic gel containing 3% w/w of a cleavable surfactant, Erucyl-SD, and 8% w/w potassium chloride, as a function of frequency (in Hz) at temperatures of 20° C., 40° C. and 60° C.

Figure 3:
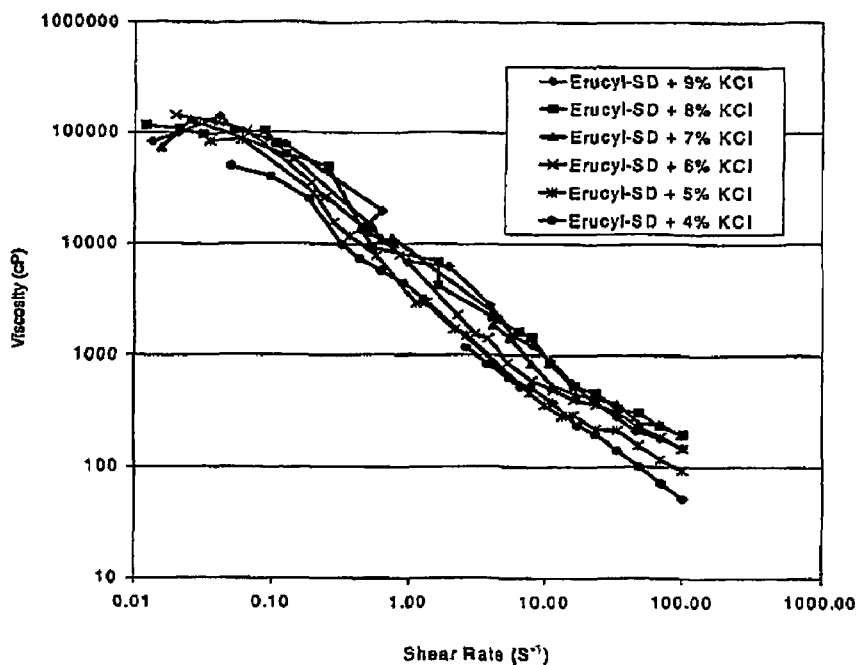
FIG. 3 is a graph of the viscosity versus shear rate (in $s^{-1}$) at 25° C. for aqueous viscoelastic compositions containing 3% w/w Erucyl-SD and varying concentrations of potassium chloride.
Figure 4:
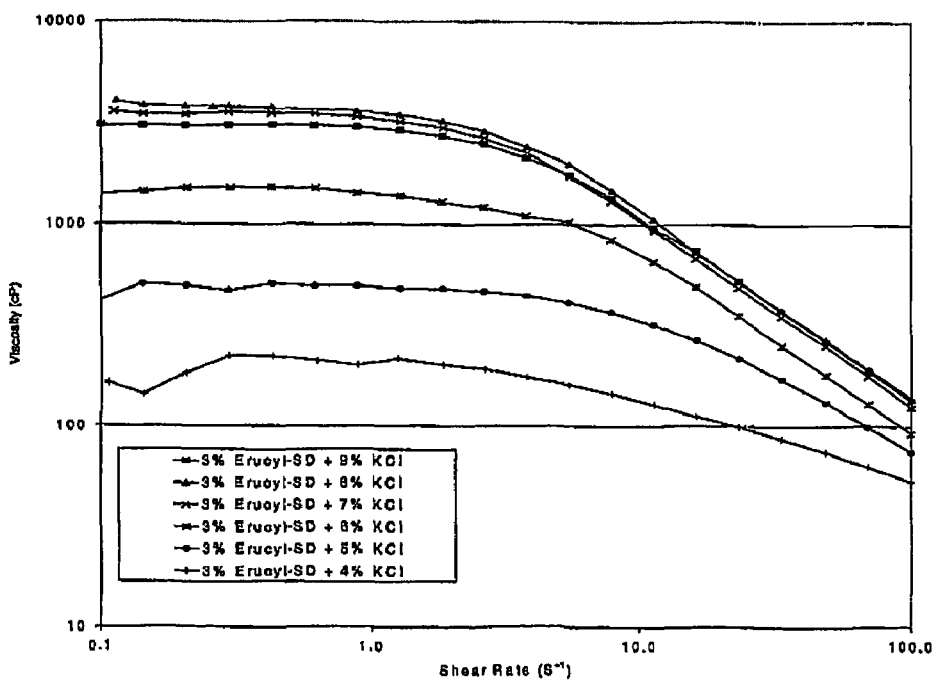
FIG. 4 is a graph similar to FIG. 3 showing results at 60° C.
Figure 5:
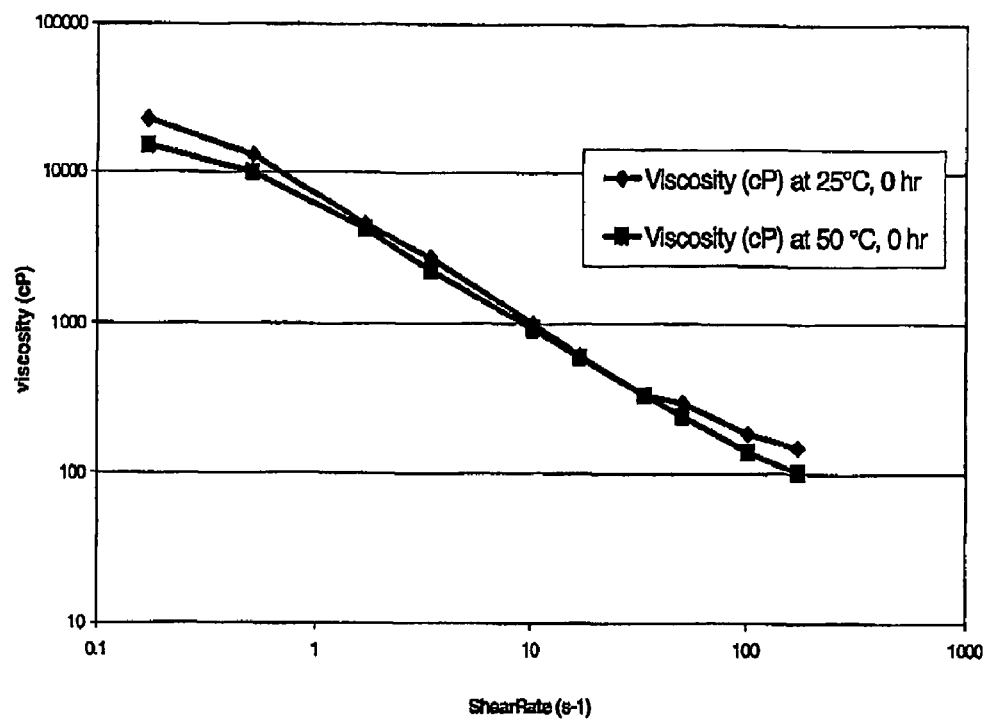

FIG. 5 is a graph similar to FIGS. 3 and 4, showing results of the viscosity profile versus shear rate for a composition containing 1.5% w/w Erucyl-SD, 0.05% w/w acetic acid, 0.5% w/w potassium acetate and 4.0% w/w potassium chloride, at 25° C. and 50° C.

Figure 6:
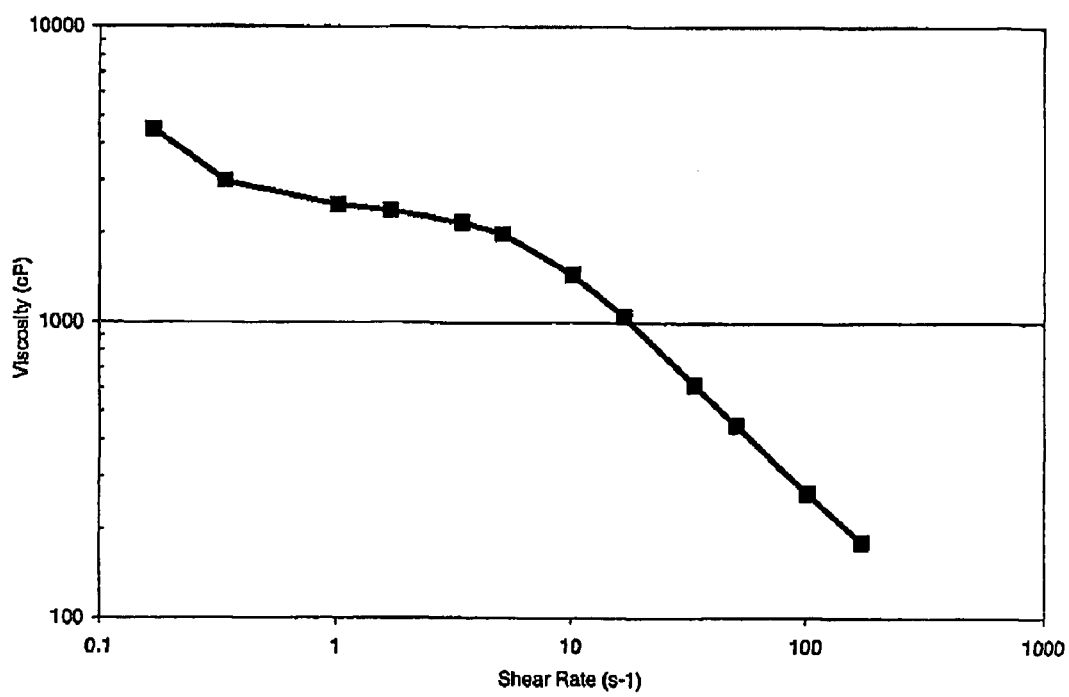

FIG. 6 is a graph of the viscosity versus shear rate at 60° C., of an aqueous viscoelastic gel containing 2.0% w/w Erucyl bis (2-hydroxyethyl)methyl ammonium chloride (EHMAC), 0.5% w/w Erucyl-SD, 0.1% w/w potassium acetate and 4.0% w/w potassium chloride.

Figure 7:
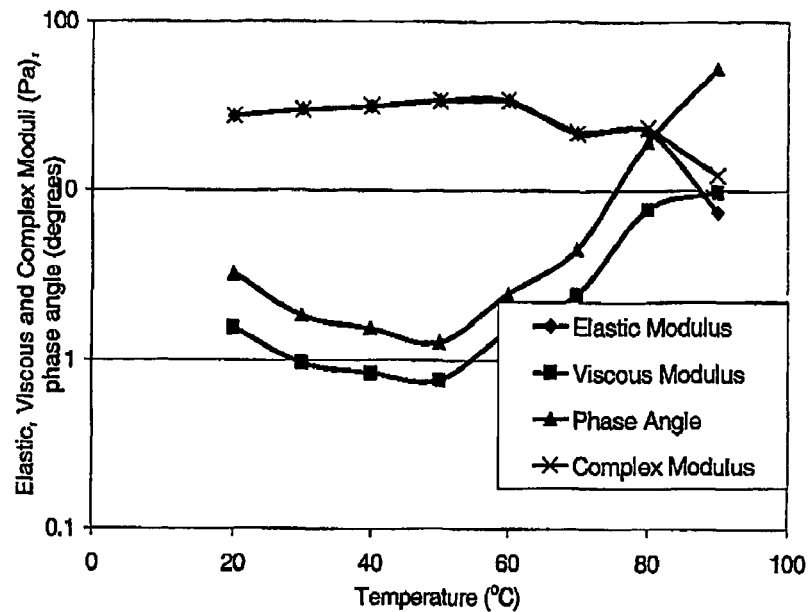

FIG. 7 is a graph of the viscoelastic properties (G' and G" measured at a frequency of 1 Hz) of an aqueous viscoelastic gel (pH 9.5) containing 4% w/w of a cleavable surfactant, MOS-SD, and 2% w/w potassium chloride as a function of temperature.

Figure 8:
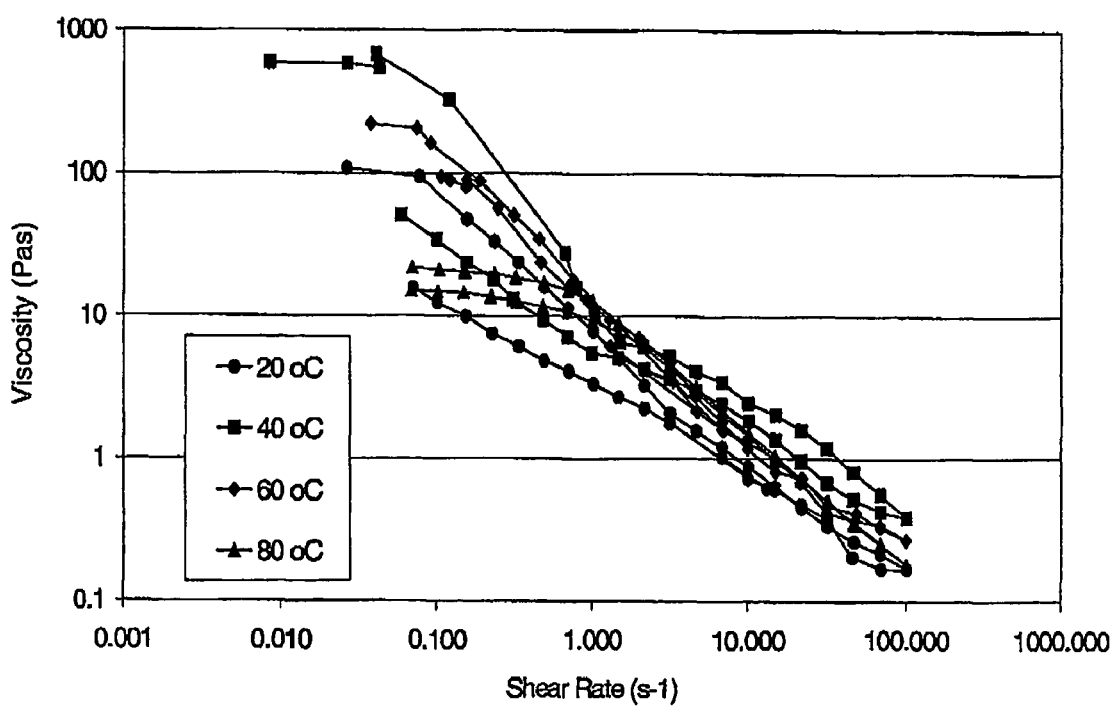

FIG. 8 is a graph of the steady shear viscosity as a function of shear rate at 20° C., 40° C., 60° C. and 80° C. respectively of a viscoelastic gel (pH 9.5) containing 4% w/w MOS-SD and 2% w/w potassium chloride.

Figure 9:
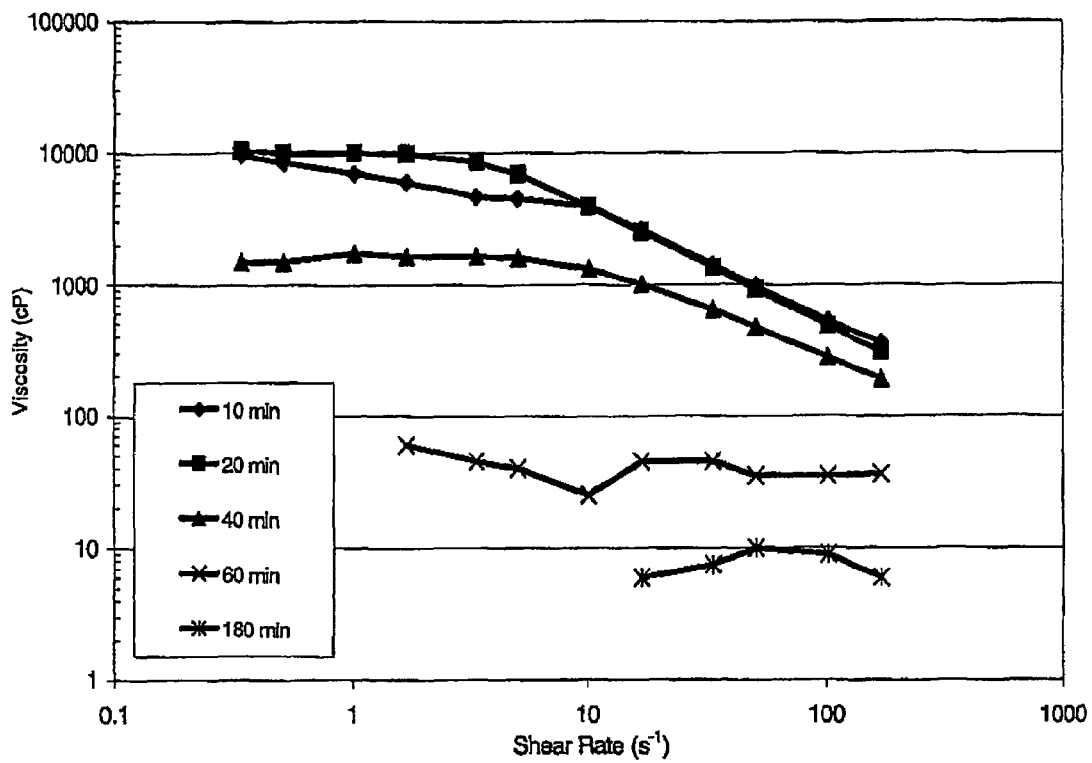

FIG. 9 is a graph of the viscosity versus shear rate over time of an aqueous viscoelastic gel containing 3% w/w Erucyl-SD, 0.6% w/w potassium acetate and 8% w/w potassium chloride measured at a temperature of 60° C.

Figure 10:
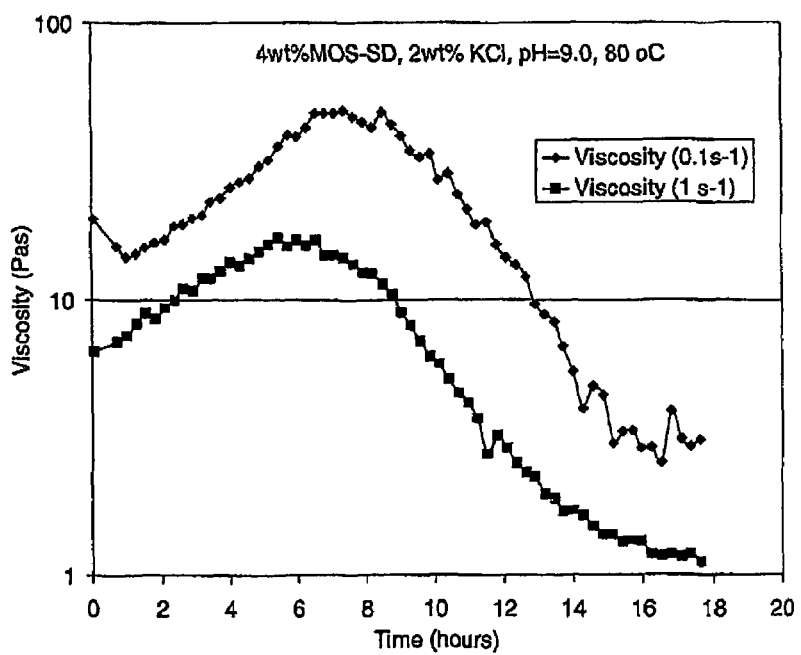

FIG. 10 is a graph illustrating the low shear viscosity profile over time of an aqueous viscoelastic gel aged at 80° C., comprising 4% w/w MOS-SD and 2% w/w potassium chloride.

Figure 11:
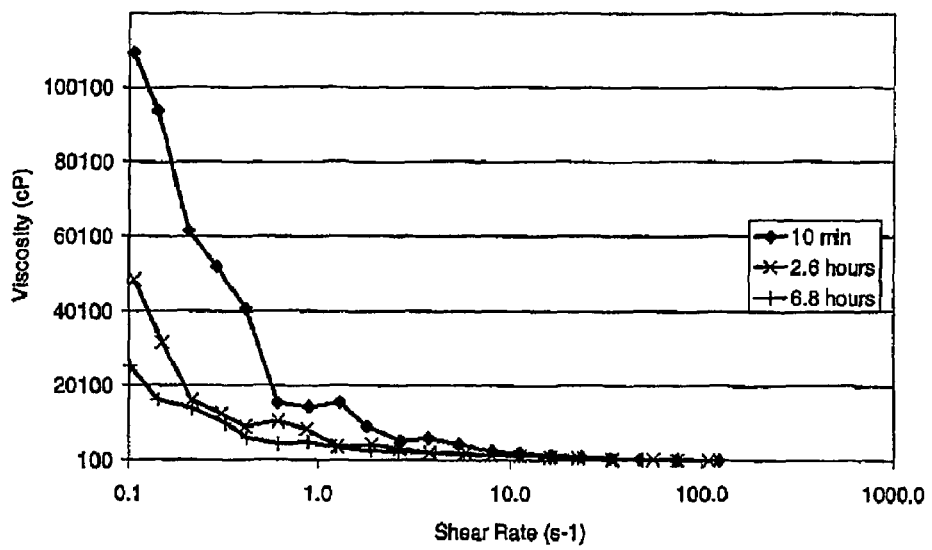

FIG. 11 is a graph similar to FIG. 9 showing the viscosity profile over time of an aqueous viscoelastic gel containing 3% w/w Erucyl-SD, 1% w/w acetic acid and 8% w/w potassium chloride measured at a temperature of 60° C.

Figure 12:
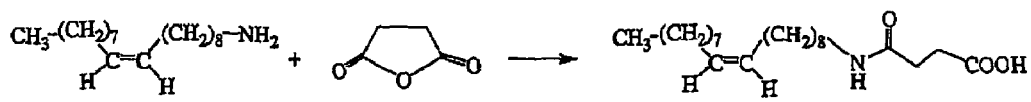

FIG. 12 shows a route for synthesis of oleyl amide succinic acid.

Figure 13:
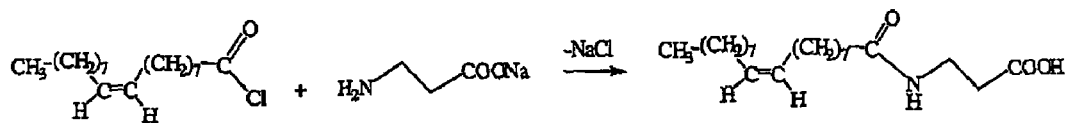

FIG. 13 shows a route for synthesis of erucyl amide succinic acid.

Figure 14:
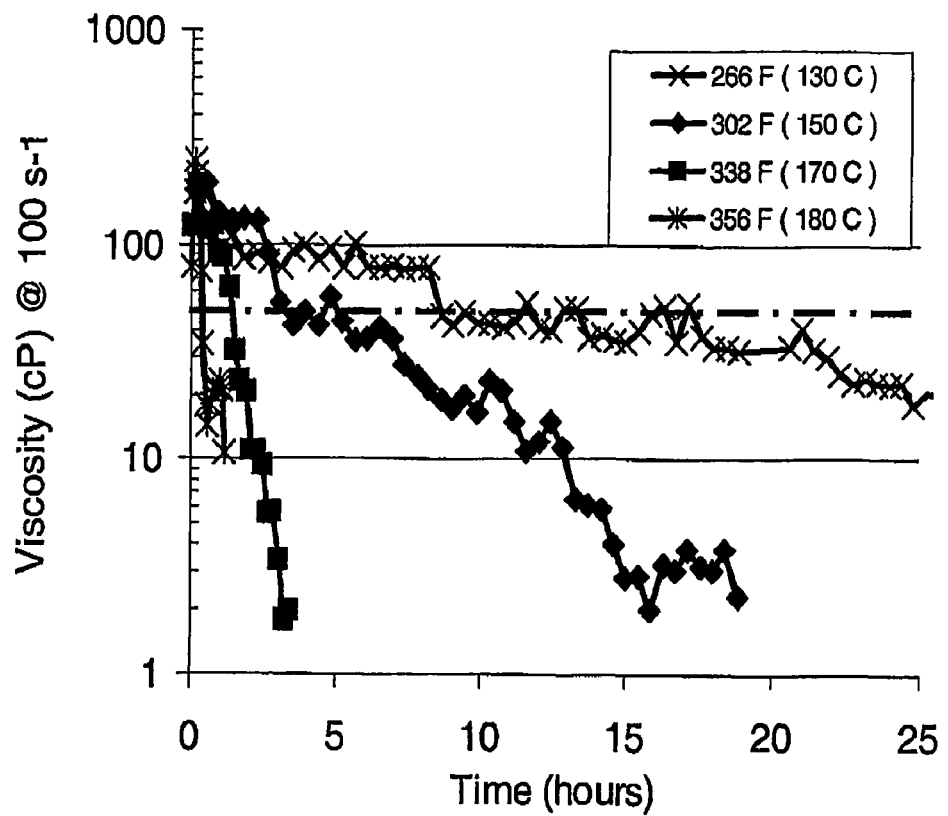

FIG. 14 compares the viscosity, at a high shear rate of 100 $s^{-1}$, of oleyl ester succinate, oleyl amide succinate and erucyl amide succinate viscoelastic gels as a function of temperature.

Figure 15:
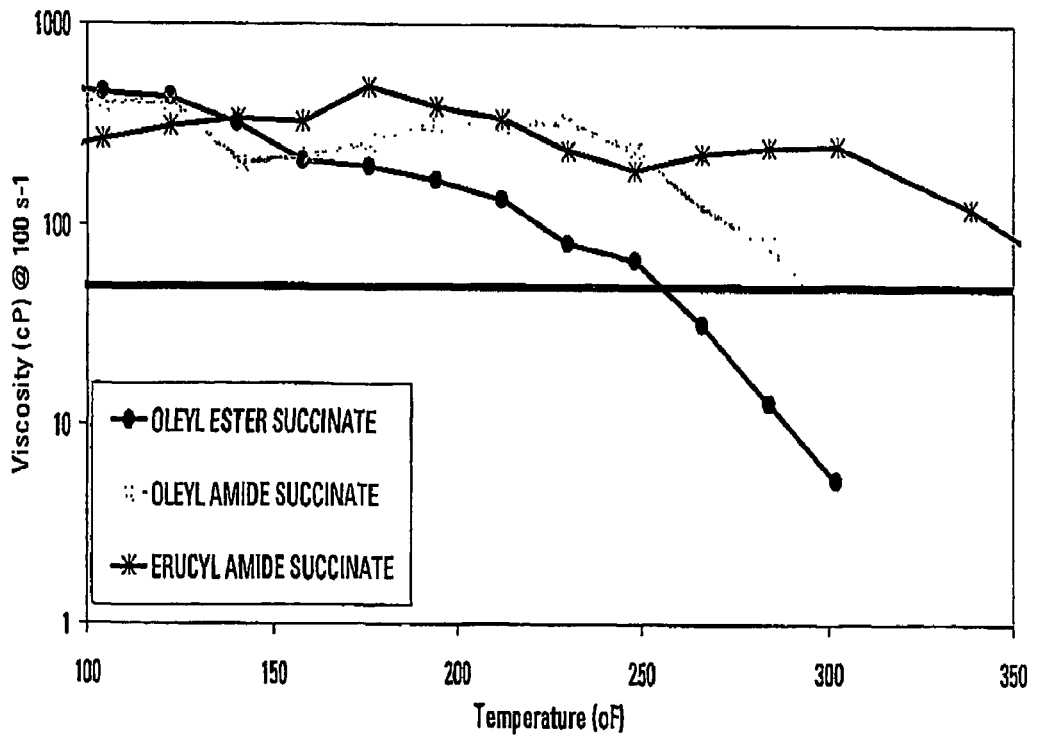

FIG. 15 compares the viscosity at a high shear rate of 100 $s^{-1}$ of a erucyl amide succinate gel over time, for various temperatures.

Figure 16:
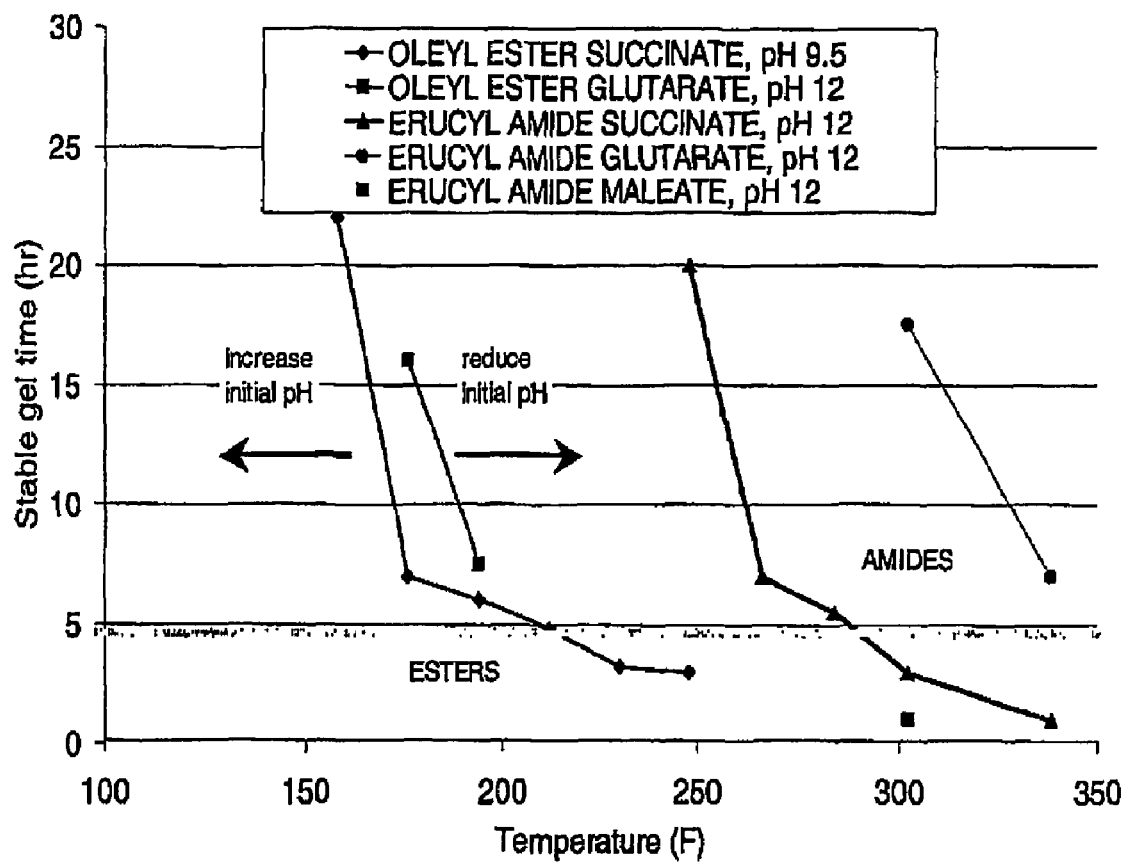

FIG. 16 compares the stability of oleyl ester succinate, oleyl ester glutarate, erucyl amide succinate, erucyl amide glutarate and erucyl amide maleate gels over temperature.

The unit of viscosity used in the Examples and in the associated Figures is centipoise (cP). One centipoise (cP) is equivalent to one millipascal second (1 mPa.s). Thus, 1000 cP=1 Pa.s.

EXAMPLE 1

Synthesis of N,N-dimethyl N-ethyl Glycine Erucyl Ester Chloride

N,N-dimethyl N-ethyl glycine erucyl ester chloride (also referred to for brevity and simplicity herein as "Erucyl-SD") was synthesised according to the reaction scheme below:

$$CH_3—(CH_2)_7 \quad (CH_2)_{11}—COOH$$
$$\diagdown C=C \diagup$$
$$\diagup \quad \diagdown$$
$$H \quad H$$
$$(1)$$
$$\xrightarrow{\text{LiAlH}_4/\text{THF}}_{0° C., 3 \text{ hrs}}$$

-continued

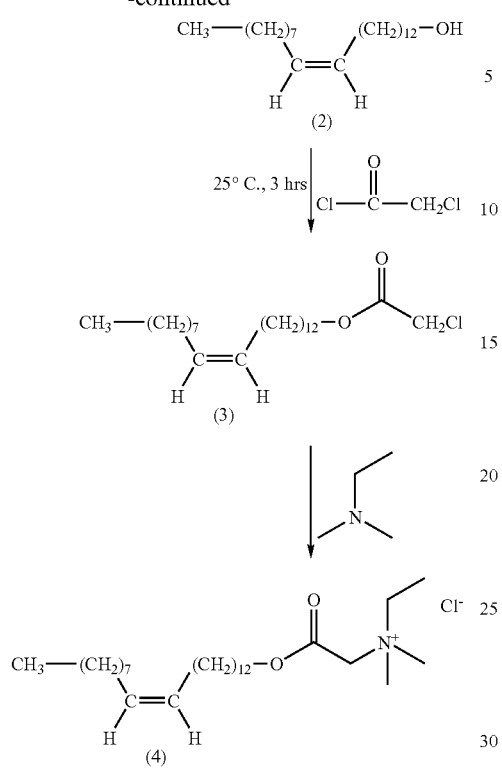

To erucic acid (1) (100 g, 295 mmol) in THF (200 ml) was slowly added LiAlH$_4$ (25.22 g, 665 mmol) with stirring. The reaction mixture was stirred at 0° C. for 3 hours. Saturated NH$_4$Cl solution (200 ml) was then added to the reaction mixture, and the organic layer collected. The aqueous layer was washed with ether (50 ml) and the ether layer separated and combined with the organic layer. The solvents of the combined organic layers were removed in vacuo to yield erucyl alcohol (2) (64.6 g, 70.9%).

To erucyl alcohol (2) (101.5 g, 310.8 mmol) in 200 ml of toluene was added chloroacetyl chloride (38.6 g, 341.9 mmol). The reaction mixture was stirred at 25° C. for 3 hours. The reaction mixture was then washed with water (100 ml) and the aqueous and organic layers separated The organic layer was dried over sodium sulphate and the solvent removed in vacuo to yield erucyl 2-chloroacetate (3) (118.7 g, 94.3%).

The conversion of erucyl 2-chloroacetate (3) to the quaternary amine, N,N-dimethyl N-ethyl glycine erucyl ester chloride (4) was carried out in THF. To a solution of erucyl 2-chloroacetate (3) (31.90 g, 79.2 mmol) in 100 ml of THF was added 6.7 g of dimethyl ethyl amine, and the reaction was stirred at 50° C. N,N-dimethyl N-ethyl glycine erucyl ester chloride (4) (29.8 g, yield: 80%) was collected as a light yellow wax by removal of the solvent (THF) in vacuo. The resulting product was washed with heptane, and dried under vacuum. The completion of the reaction was monitored using thin layer chromatography (TLC).

The reaction intermediates (2) and (3) and product (4) were characterized by mass spectroscopy and thin layer chromatography.

The product, N,N-dimethyl N-ethyl glycine erucyl ester chloride (4) was a waxy solid at room temperature and soluble in water.

EXAMPLE 2

Preparation of an Aqueous Viscoelastic Gel of N,N-dimethyl N-ethyl Glycine Erucyl Ester Chloride (Erucyl-SD) with 8% w/w Potassium Chloride.

The viscoelastic properties of a gel depend on the concentration of the cleavable surfactant, temperature, and the type and concentration of added electrolyte.

An aqueous viscoelastic gel composition was obtained by adding 8% w/w of potassium chloride (KCl) to an aqueous solution of 3% w/w of Erucyl-SD.

Figure 1:
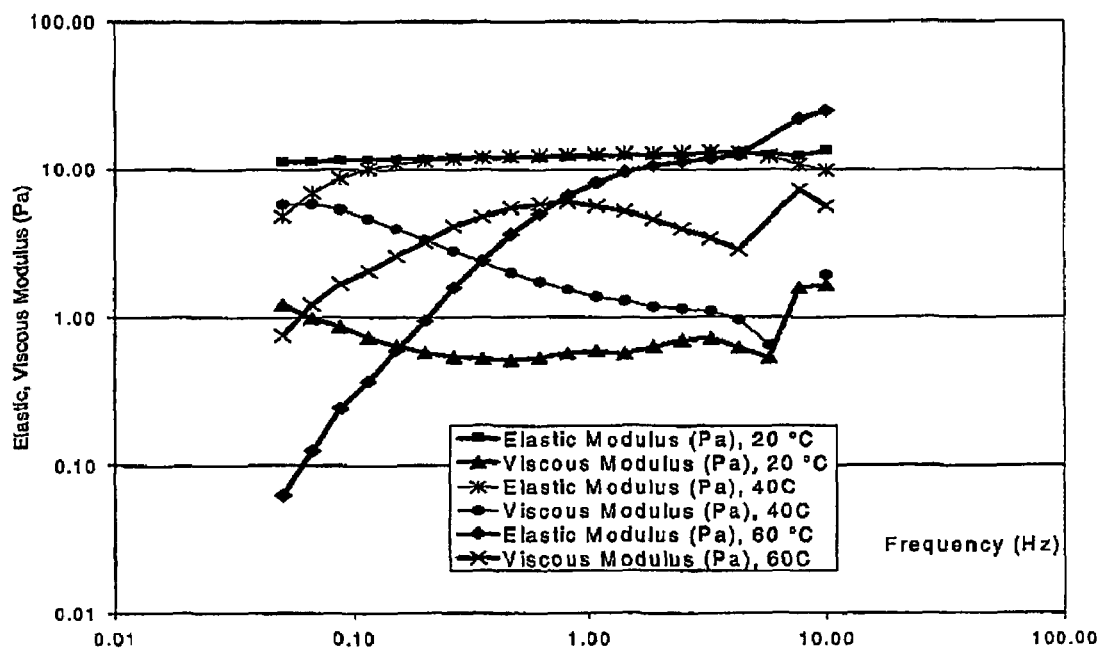
Figure 2:
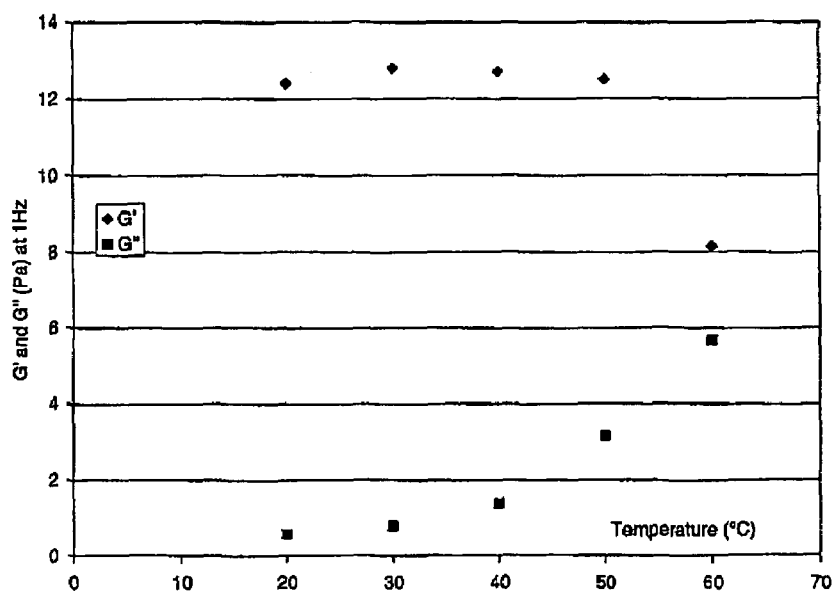
FIG. 2 is a graph showing the viscoelastic properties, particularly the elastic modulus (G') and the viscous modulus (G") measured at a frequency of 1 Hz for an aqueous viscoelastic gel containing 3% w/w of a cleavable surfactant, Erucyl-SD, and 8% w/w potassium chloride as a function of temperature.

FIGS. 1 and 2 demonstrate the viscoelastic properties of the above composition in the temperature range 20° C. to 60° C. The data was obtained using a controlled stress rheometer (model types CVO-50, CVO-120 or CS50 available from Bohlin Instruments), fitted with standard couette (cup and bob) geometry (C25).

FIG. 1 demonstrates the results of dynamic oscillatory experiments performed to determine the elastic or storage modulus G' (the elastic component) and the viscous or loss modulus G" (the viscous component) of the sample as a function of oscillation frequency (0.05-10 Hz) at constant strain 0.1.

At 20° C., the composition takes the form of a strong elastic gel. Throughout the measured frequency range 0.05-10 Hz, the elastic modulus, G' (11.3-12.4 Pa) is around one order of magnitude higher than the viscous modulus, G", suggesting that the sample behaves like an elastic solid with a long relaxation time, $t_R$>>20 s. At 40° C., the same sample exhibits viscoelastic behaviour such that when the frequency is <0.06 Hz, G">G' and when the frequency is >0.06 Hz, G'>G". Thus, at 40° C. the relaxation time, $t_R$, can be determined as 17 s, and there is a terminal region in the frequency spectrum indicating a plateau in the viscosity at very low shear rates. At 60° C., the sample again exhibits viscoelastic behaviour with a reduced relaxation time, $t_R$=1.4 s. Thus, when T≧40° C., the rheology of the fluid becomes characteristic of a Maxwell fluid with a single relaxation time, $t_R$; the dynamic moduli can then be described by:

$$G'(\omega)=(G_p\omega^2 t_R^2)/(1+\omega^2 t_R^2) \text{ and } G''(\omega)=(G_p\omega t_R)/(1+\omega^2 t_R^2)$$

The zero-shear viscosity of a Maxwell fluid is given by:

$$\eta_0 = G_p t_R$$

where $G_p$ is a plateau value of G'. From FIG. 1, it will be appreciated that $G_p$ is essentially independent of temperature and the zero-shear viscosity of the sample can be estimated as >>240,000 cP at 20° C., 200,000 cP at 40° C. and 17160 cP at 60° C.

FIG. 2 is a plot of the dynamic moduli measured at a single frequency (1 Hz) versus temperature. The data demonstrates that the elastic modulus of the sample is greater than the viscous modulus from ambient temperature to elevated temperatures above 60° C.

EXAMPLE 3

Determination of Shear Viscosity as a Function of Shear Rate for Compositions Containing N,N-dimethyl N-ethyl Glycine Erucyl Ester Chloride with Varying Concentrations of Potassium Chloride.

Six compositions containing 3% w/w Erucyl-SD and 4, 5, 6, 7, 8 and 9% w/w potassium chloride (KCl) respectively were prepared. The steady shear viscosities as a function of shear rate of each of the compositions was measured at 25° C. and 60° C. The results of the measurements are shown in FIGS. 3 and 4.

As in Example 2, the data was collected using a controlled stress rheometer fitted with standard couette (cup and bob) geometry (C25).

At 25° C. (FIG. 3), the data for the compositions with 5-9% w/w KCl suggested that the viscosity reaches a maximum (Newtonian plateau) in the low shear rate range 0.01-0.1 s$^{-1}$. The apparent maximum in the viscosity is in the range 100000-200000 cP. This is in reasonable agreement with the zero shear viscosity, $\eta_0$, given by the product of the plateau elastic modulus $G_p$, and the relaxation time, $t_R$, determined from dynamic oscillatory measurements in Example 2 using the same couette geometry.

At 60° C. FIG. 4), the same compositions show a clearly defined Newtonian plateau in the lower shear rate range. A maximum in the Newtonian plateau viscosity (around 4000 cP) is observed when the composition contains 8 wt % KCl.

EXAMPLE 4

The following composition was prepared and the viscosity of said composition was measured at 25° C. and 50° C. at varying shear rates:

| | |
|---|---|
| Erucyl-SD (prepared as illustrated in Example 1) | 1.5% w/w |
| Acetic Acid | 0.5% w/w |
| Potassium Acetate | 0.5% w/w |
| Potassium Chloride | 4.0% w/w |
| Water | to 100% |

The results of the steady-shear viscosity of the composition measured for a particular shear rate are shown in FIG. 5. FIG. 5 shows the composition having a low shear viscosity>10000 cP at both 25° C. and 50° C.

EXAMPLE 5

The cleavable surfactant, Erucyl-SD (prepared in Example 1), can also be utilised to create a viscoelastic gel in combination with other cationic viscoelastic surfactants such as erucyl bis(2-hydroxyethyl) methyl ammonium chloride EHMAC).

The following aqueous viscoelastic gel was prepared and the viscosity of said gel was measured at 60° C. at varying shear rates:

| | |
|---|---|
| Erucyl-SD | 0.5% w/w |
| Erucyl bis(2-hydroxyethyl)methyl ammonium chloride | 2.0% w/w |
| Potassium Acetate (KOAc) | 0.1% w/w |
| Potassium Chloride | 4.0% w/w |
| Water | to 100% |

The results of these measurements are indicated in FIG. 6.

Generally it is observed that the viscoelastic properties exhibited by a composition comprising both a cleavable and a non-cleavable surfactant can be usefully enhanced relative to equivalent compositions containing the same or possible higher concentrations of either type of surfactant alone. Furthermore, the combination of a cleavable surfactant such as Erucyl-SD with a non-cleavable surfactant such as EHMAC provides a viscoelastic gel which is capable of being degraded to a low viscosity solution under the appropriate conditions when erucyl alcohol, released by the cleavage of the Erucyl-SD surfactant, destroys the viscoelasticity imparted to the gel by the EHMAC surfactant.

EXAMPLE 6

Synthesis of Monooleyl Succinic Acid

The cleavable surfactant, monooleyl succinic acid (referred to herein for brevity and simplicity as 'MOS-SD'), having a structure as shown below was synthesised according to the following procedure:

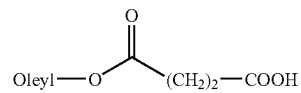

To a solution of oleyl alcohol (99.4 g, 370 mmol) in tetrahydrofuran (THF) (400 ml) was added succinic anhydride (44.4 g, 444 mmol), followed by dimethylethyl amine (32.5 g, 444 mmol). The reaction mixture was stirred at 40° C. for 3 hours after which the THP solvent was removed in vacuo resulting in the formation of a light yellow oil. The oil was then acidified to pH 5 with a 2 molar solution of hydrochloric acid (100 ml) and the resulting product extracted with ether (3×100 ml). The combined ether layers were then removed in vacuo to yield the monooleyl succinic acid product (109 g, 80%). Deprotonation of monooleyl succinic acid produces monooleyl succinate.

Analysis by mass spectroscopy confirms the expected molecular weight of the product, monooleyl succinic acid (368 g/mol).

Mass Spectroscopy m/z 386 (MH$_2$O).

EXAMPLE 7

Preparation of an Aqueous Viscoelastic Gel of Monooleyl Succinate (MOS-SD)

An aqueous solution containing 4% w/w MOS-SD surfactant was prepared using deionised water with the addition of potassium hydroxide until the solution attained a pH of 9.5. The addition of 2% w/w of potassium chloride to the latter solution resulted in the formation of a strong aqueous viscoelastic gel.

FIG. 7 demonstrates the viscoelastic properties of this gel as a function of temperature. It is notable that, in this case, the viscoelastic gel maintains an elastic modulus, G', which is greater than the viscous modulus, G", throughout the temperature range 20-88° C.

FIG. 8 shows the steady shear viscosity as a function of shear rate for the aqueous viscoelastic gel prepared above at the temperatures, 20, 40, 60 and 80° C., respectively. The Figure demonstrates that the low shear viscosity of the gel reaches a maximum (>100,000 cP) in the temperature range 40-50° C. This is consistent with a maximum in the ratio G'/G" given by the dynamic oscillatory measurements (FIG. 7). The viscoelastic gel maintains a low shear (0.1-1s$^{-1}$) viscosity well in excess of 10000 cP at 80° C. (FIG. 8). The data shown in FIGS. 7 and 8 was again collected using a controlled stress rheometer fitted with standard couette (cup and bob) geometry (C25).

EXAMPLES 8 AND 9

Decomposition of Erucyl-SD Under Alkaline Conditions

An aqueous viscoelastic gel was prepared according to the following formulation:

|  | % w/w |
|---|---|
| Erucyl-SD | 3.0 |
| Potassium Chloride | 8.0 |
| Water | to 100 |

When a 1 molar solution of sodium hydroxide was added to the aqueous viscoelastic gel prepared as described above at ambient temperature, the gel was almost immediately degraded. After only 3 minutes, the aqueous viscoelastic gel was converted to a clear solution with a water-like viscosity with solid erucyl alcohol floating on the surface. The latter product will not form an emulsion when vigorously mixed with an excess of oil. The reaction is shown below;

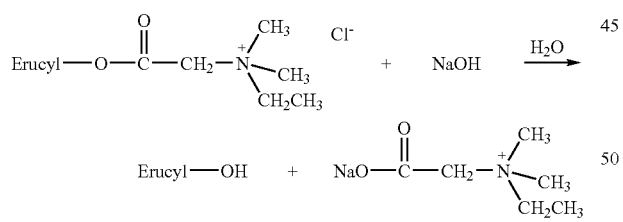

A further aqueous viscoelastic gel of initial pH 8.1 was prepared according to the following formulation:

|  | % w/w |
|---|---|
| Erucyl-SD | 3.0 |
| Potassium Chloride | 8.0 |
| Potassium Acetate | 0.6 |
| Water | to 100 |

The gel was aged at 60° C. and the viscosity monitored as a function of time. The results are shown in FIG. 9 where the aqueous viscoelastic gel is reduced to a solution with viscosity <10 cP after 180 minutes. The latter solution will not form an emulsion when vigorously mixed with oil.

EXAMPLE 10

Decomposition of MOS-SD Under Alkaline Conditions

An aqueous viscoelastic gel of initial pH 9.0 was prepared according to the following formulation:

|  | % w/w |
|---|---|
| MOS-SD (prepared in Example 6) | 4.0 |
| Potassium chloride | 2.0 |
| Water | to 100 |

The gel was aged at 80° C. and the viscosity monitored as a function of time. The results are shown in FIG. 10 where in this case, the strong aqueous viscoelastic gel is reduced to a low viscosity solution after 16-20 hours. The latter solution will not form an emulsion when vigorously mixed with oil. The rate of decomposition or cleavage of the MOS-SD surfactant can be increased by increasing the initial pH of the gel. FIG. 10 also illustrates that the low shear viscosity of the MOS-SD gel initially increases in the time interval t=0 to t=6 hours (approx.) before decreasing sharply during the period from t=6 hours (approx) to t=16 hours (approx.).

EXAMPLE 11

Decomposition of Erucyl-SD Under Acidic Conditions

An aqueous viscoelastic gel was prepared according to the following formulation:

|  | % w/w |
|---|---|
| Erucyl-SD | 3.0 |
| Potassium Chloride | 8.0 |
| Acetic Acid | 1.0 |
| Water | to 100 |

The gel was aged at 60° C. and the viscosity monitored as a function of time. The results are shown in FIG. 11, where the viscosity of the gel progressively decreases during the 7 hour ageing period. The reaction is shown below:

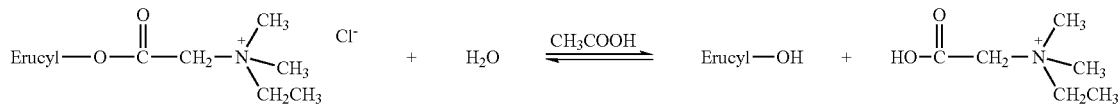

EXAMPLE 12

Synthesis of Amide Carboxylates Cleavable Surfactants

Oleyl amide succinic acid was synthesised using the following procedure. To a solution of 50 of oleyl amine in 100 ml THF was added 22 g, that is to say 1.2 mole equivalents, of succinic anhydride. The solution was then refluxed at a temperature of 68° C. for 48 hours to ensure the complete reaction shown in the FIG. 12. THF was removed under vacuum and 50 ml of petroleum ether was added. The excess succinic anhydride not soluble in petroleum ether was removed by filtration on Whatman paper 43. The petroleum ether solution was cooled down and maintained at −10° C. overnight using a refrigerated centrifuge. The white solid was then collected by centrifuging for 30 min at 9000 rpm. The product was washed with cold petroleum ether and dried under vacuum.

An equivalent procedure was used to prepare oleyl amide maleic acid form maleic acid and oleyl amide glutaric acid from glutaric anhydride.

EXAMPLE 13

Synthesis of Forward Amide carboxylates Cleavable Surfactants

The reagent erucyl acid chloride was prepared from erucic acid in the following manner. To 50 g erucic acid in 20 ml of THF was added 50 ml thionyl chloride. The reaction was continued under reflux for 30 min and the solvent was removed under vacuum. A light brown liquid, the erucyl acid chloride product, was collected. To this liquid was added a solution/suspension of the sodium salt of beta-alanine in THF. The reaction shown in the FIG. 13 then took place under reflux for 24 hours. The solvent was removed under vacuum and petroleum ether was added. The solution was filtered on Whatman paper 43 and the filtrate solution was then cooled down to −10° C. A light yellow solid product was collected

EXAMPLE 14

Decomposition of Erucyl Amide Succinate and Erucyl Amide Glutarate Under Temperature On FIG. 14 is plotted the viscosity, at a shear rate of 100 s$^{-1}$, of an aqueous viscoelastic fluid according to the invention comprising 4 wt % of erucyl amide succinate and 4 wt % KCl, at a pH equal to 12, as a function of time, for the following temperatures: 130° C., 150° C., 170° C. and 180° C. A horizontal doted line is positioned at about 50 cP on FIG. 14. It defines the limit at which the gel is considered to be insufficient for fracturing applications.

At 180° C., the gel breaks in less than 1 hour. At 170° C., the gel breaks in about 2 hours. At 150° C. however, the viscosity of the gel decreases along time. It breaks in about 4-6 hours to reach a viscosity of about 2 cP at about 15 hours. Finally, at 130° C., the viscosity decreases very slowly is still in excess of 50 cP after 5 hours. After 25 hours, the viscosity is still greater than about 20 cP.

As a consequence, a fluid comprising erucyl amide succinate may be used notably for fracturing applications between about 260° F. and about 360° F. Under 260° F., it will not degrade significantly and, above 360° F., it will degrade too rapidly to permit the transport of the propping agent and to prevent the fracture from closing.

Other experiments have been made under the same conditions that above with a gel comprising erucyl amide glutarate. These experiments permitted to show that a viscoelastic gel comprising erucyl amide glutarate may be used for fracturing applications above 300° F.

No emulsion tendency when mixed with oil was found in the degraded fluids.

EXAMPLE 15

Comparison of the Rheology of Aqueous Viscolestic Fluids Comprising N-erucyl-N,N-bis(2-hydroxyethyl)-N-methyl Ammonium Chloride, Oleyl Ester Succinate, Oleyl Amide Succinate or Erucyl Amide Succinate Over the Temperature On the FIG. 15 is plotted the viscosity, at a high shear rate of 100 s$^{-1}$, of viscoelastic fluids comprising N-erucyl-N,N-bis(2-hydroxyethyl)-N-methyl ammonium chloride, oleyl ester succinate, oleyl amide succinate or erucyl amide succinate, as a function of temperature. The horizontal line indicates the level at which the gel is considered to be insufficient for fracturing aplication.

It appears that the viscosity of erucyl-N,N-bis(2-hydroxyethyl)-N-methyl ammonium chloride gel falls at a temperature of about 180° F. (82° C.). The oleyl ester succinate, oleyl amide succinate and erucyl amide succinate gels remain stable at 250° F. (121.1° C.). Amongst those gels, the erucyl amide succinate remains stable at higher temperatures than those of the oleyl ester and oleyl amide succinate gels. Practically, the oleyl ester succinate degrades at temperatures of about 260° F. (126.7° C.), the oleyl amide gel degrades at temperatures of about 290° F. (143.3° C.) and the erucyl amide succinate gel degrade at temperature greater than 350° F. (176.7° C.).

No emulsion tendency when mixed with oil was found in the degraded fluids containing oleyl ester succinate, oleyl amide succinate or erucyl amide succinate.

EXAMPLE 16

Comparison of the Degradation Rate of Viscoelastic Gels Comprising Oleyl Ester Succinate, Oleyl Ester Glutarate, Erucyl Amide Succinate, Erucyl Amide Glutarate and Erucyl Amide Maleate Aqueous viscoelastic surfactant fluids comprising, either, oleyl ester succinate, oleyl ester glutarate, erucyl amide succinate, erucyl amide glutarate or erucyl amide maleate were prepared. The pH of these fluids is equal to, respectively, 9.5, 12, 12, 12 and 12. On the FIG. 16 is plotted the period of time during which the gel is stable as a function of the temperature. A horizontal line figures the 5 hours period of time in which it is advantageous to have a gel stable for fracturing applications.

It appears that the oleyl ester succinate viscoelastic gel remain stable approximately 4 hours between about 150 (65.56° C.) and about 250° F. (121.1° C.). An increase in the fluid initial pH would have slightly displaced the curve obtained for the oleyl ester succinate viscoelastic gel on the left, that is to say towards lower temperatures. Therefore, it is estimated that, oleyl ester succinate viscoelastic gels, controlled by their pH, remain stable approximately 4 hours between approximately 4 hours between about 120 (48.89° C.) and about 250° F. (121.1° C.).

The oleyl ester glutarate viscoelastic gel remains stable more than 5 hours between about 175 (79.44) and about 200° F. (93.33° C.). A reduction in the fluid initial pH would have slightly displaced the curve on the right that is to say towards greater temperature. Therefore, it is estimated that oleyl ester glutarate viscoelastic gels, controlled by their pH, remain stable more than 5 hours between about 175 (79.44) and 220° F. (104.4° C.).

The erucyl amide succinate viscoelastic gel remains stable more than 4-5 hours between about 250 (121.1) and about 300° F. (148.9° C.). Then, this gel may be used for fracturing applications between these temperatures.

The erucyl amide glutarate viscoelastic gel remains stable more than 5 hours between about 300 (148.9) and about 350° F. (176.7° C.). Then, this gel may be used for fracturing applications between these temperatures.

Finally, the aqueous viscoelastic surfactant gels comprising oleyl ester succinate, oleyl ester glutarate, erucyl amide succinate and erucyl amide glutarate are all stable, more than 4-5 hours, at high temperatures. Whatever be the temperature at downhole location in the range 120 to 350° F., it is possible to use one the above gel. These form a family of fluids that can be used.

The invention claimed is:

1. A wellbore service fluid, comprising: an aqueous viscoelastic composition that comprises cleavable surfactant, the cleavable surfactant comprising a reverse amide surfactant or a reverse ester surfactant and having the structure of formula 1, formula 2 or formula 3:

  Formula 1 or

  Formula 2 or

  Formula 3 where (i) $R_1$ is a saturated or unsaturated, linear or branched aliphatic chain of at least 18 carbon atoms;
(ii) X is an —, or $R_7N(CO)$ group;
(iii) m is at least one;
(iv) $Y^\oplus$ is $-NR_2R_3R_4$;
(v) $R_2, R_3, R_4, R_5, R_6$ and $R_7$ are each independently hydrogen; a linear or branched, saturated aliphatic chain of at least 1 carbon atom; or a linear or branched, saturated aliphatic chain of at least 1 carbon atom with one or more of the hydrogen atoms replaced by a hydroxyl group;
(vi) $A^\ominus$ is a sulfonate or carboxylate anionic group;
(vii) $Z^\ominus$ and $B^\oplus$ are ionic counterions associated with a cleavable surfactant of formula 1 or formula 2, where $Z^\ominus$ is a monovalent anion or divalent anion and $B^\oplus$ is hydrogen or a monovalent cation;

wherein:
the cleavable surfactant is cleavable at the group X into breakdown products that are soluble in oil or water and include the alcohol $R_1$—OH or the amine $R_1$—$NHR_7$; and
the cleaving of the cleavable surfactants into the oil or water soluble breakdown products removes viscoelastic and viscosifying properties of the wellbore service fluid and reduces potential for the wellbore service fluid to form emulsions.

2. A wellbore service fluid according to claim 1, wherein the cleavable surfactant is N, N-dimethyl N-ethyl glycine erucyl ester chloride.

3. A wellbore service fluid according to claim 1, wherein the cleavable surfactant is the monooleyl ester of succinic acid.

4. The wellbore service fluid according to claim 1, further comprising an electrolyte.

5. The wellbore service fluid according to claim 4, wherein the electrolyte comprises at least one inorganic water soluble salt or organic water soluble salt, or mixtures thereof.

6. The wellbore service fluid according to claim 1, wherein the aqueous viscoelastic composition comprises an aqueous viscoelastic gel.

7. A wellbore service fluid, comprising: an aqueous viscoelastic composition that comprises an anionic or cationic cleavable surfactant, the anionic or cationic cleavable surfactant having the structure of formula 1 or formula 2:

  Formula 1 or

  Formula 2 where (i) $R_1$ is a saturated or unsaturated, linear or branched aliphatic chain of at least 18 carbon atoms;
(ii) X is an O(CO), or $R_7N(CO)$ group;
(iii) m is at least two;
(iv) $Y^\oplus$ is $-NR_2R_3R_4$;
(v) $R_2, R_3, R_4, R_5, R_6$ and $R_7$ are each independently hydrogen; a linear or branched, saturated aliphatic chain of at least 1 carbon atom; or a linear or branched, saturated aliphatic chain of at least 1 carbon atom with one or more of the hydrogen atoms replaced by a hydroxyl group;
(vi) $A^\ominus$ is a sulfonate or carboxylate anionic group;
(vii) $Z^\ominus$ and $B^\oplus$ are ionic counterions associated with a cleavable surfactant of formula 1 or formula 2, where $Z^\ominus$ is a monovalent anion or divalent anion and $B^\oplus$ is hydrogen or a monovalent cation;

wherein:
the anionic or cationic cleavable surfactant is cleavable at the group X into breakdown products that are soluble in oil or water and include the alcohol $R_1$—OH or the amine $R_1$—$NHR_7$; and
the cleaving of the cleavable surfactants into the oil or water soluble breakdown products removes viscoelastic and viscosifying properties of the wellbore service fluid and reduces potential for the wellbore service fluid to form emulsions.

8. The wellbore service fluid according to claim 7, further comprising an electrolyte.

9. The wellbore service fluid according to claim 8, wherein the electrolyte comprises at least one inorganic water soluble salt or organic water soluble salt, or mixtures thereof.

10. The wellbore service fluid according to claim 7, wherein the aqueous viscoelastic composition comprises an aqueous viscoelastic gel.

11. A wellbore service fluid, comprising:

an aqueous viscoelastic composition comprising a cleavable surfactant forming rod-shaped or worm-like micelles and which is cleavable into breakdown products that are soluble in oil or water, wherein the cleavable surfactant comprises a reverse amide surfactant or a reverse ester surfactant having the formula $$R_1\text{—X-T}$$

wherein
(i) $R_1$ is a hydrophobic saturated or unsaturated, linear or branched aliphatic chain of at least 18 carbon atoms;
(ii) X is an O(CO) or $R_7$N(CO) group;
(iii) T is an anionic, cationic or zwitterionic group;
wherein the cleaving of the cleavable surfactant at the group X into the oil or water soluble breakdown products which include the alcohol $R_1$—OH or the amine $R_1$—$NHR_7$ removes viscoelastic and viscosifying properties of the wellbore service fluid and reduces potential for the wellbore service fluid to form emulsions.

12. The wellbore service fluid according to claim 11, wherein the cleavable surfactant is anionic or cationic.

13. The wellbore service fluid according to claim 11, wherein the weak chemical bond of the cleavable surfactant is cleaved to produce at least one oil soluble product and at least one water soluble product.

14. The wellbore service fluid according to claim 11, further comprising an electrolyte.

15. The wellbore service fluid according to claim 14, wherein the electrolyte comprises at least one inorganic water soluble salt or organic water soluble salt, or mixtures thereof.

16. The wellbore service fluid according to claim 11, wherein the aqueous viscoelastic composition comprises an aqueous viscoelastic gel.

* * * * *